United States Patent
Bazan et al.

(10) Patent No.: US 6,566,359 B1
(45) Date of Patent: May 20, 2003

(54) 2,4,6-TRIMETHYL-1,4-DIHYDRO-PYRIDINE-3,5-DICARBOXYLIC ACID ESTERS AS NEUROPROTECTIVE DRUGS

(75) Inventors: Nicholas G. Bazan, Baton Rouge, LA (US); Carlos Sunkel, Madrid (ES); Victor L. Marcheselli, Covington, LA (US); Julio Builla-G., Madrid (ES)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/151,984

(22) Filed: May 20, 2002

(51) Int. Cl.⁷ ................... A61K 31/5377; A61P 25/28; C07D 413/14
(52) U.S. Cl. ................... 514/232.2; 544/82; 546/272.7; 546/321
(58) Field of Search ................... 544/82; 546/321; 514/232.2

(56) References Cited

U.S. PATENT DOCUMENTS

| | | |
|---|---|---|
| 3,974,275 A | 8/1976 | Bossert et al. |
| 3,996,234 A | 12/1976 | Bossert et al. |
| 4,755,512 A | 7/1988 | Poindexter et al. |
| 4,788,205 A | 11/1988 | Cooper et al. |
| 4,801,598 A | 1/1989 | Cooper et al. |
| 4,937,242 A | 6/1990 | Matsui et al. |
| 5,068,337 A | 11/1991 | Archibald et al. |
| 5,070,205 A | 12/1991 | Cooper et al. |
| 5,177,211 A | 1/1993 | Sunkel et al. |

FOREIGN PATENT DOCUMENTS

| | | |
|---|---|---|
| EP | 0 325 187 | 1/1989 |
| WO | 90/12015 | 10/1990 |

OTHER PUBLICATIONS

Aveldano, M.I. et al., Differential lipid deacylation during brain ischemia in a homeotherm and a poikotherm. Content and composition of free fatty acids and triacylglycerols, Brain Res., vol. 100, pp. 99–110 (1975).

Bazan, N.G. et al., "Platelet activating factor in the modulation of excitatory amino acid neurotransmitter release and of gene expression," J. Lipid Mediat. Cell Signal, vol. 14, pp. 321–330 (1996a).

Bazan, N.G. et al., "Platelet–activating factor and retinoic acid synergstically activate the inducible prostaglandin synthase gene," Proc. Natl. Acad. Sci., vol. 91, pp. 5252–5256 (1994).

Bazan, N.G., "Changes in free fatty acids of brain by drug induced convulsions, electroshock and anesthesia," J. Neurochem., vol. 18, pp. 1379–1385 (1971). Bazan 1971.

Bazan, N.G., "Effects of ischemia and electroconvulsive shock on free fatty acid pool in the brain," Biochim. Biophys. Acta, vol. 218, pp. 1–10 (1970).

Bazan, N.G. "Inflammation: A signal terminator," Nature, vol. 374, pp. 501–502 (1995).

Bazan, N.G. et al., "Endogenous pools of arachidonic acid enriched membrane lipids in cryogenic brain edema," In: Recent Progress in the Study of Brain Edema, (K.G. Go and A. Baethmann, eds), Plenum Press, New York, pp 203–212 (1984).

Bazan, N.G. et al., "Free arachidonic acid and membrane lipids in the central nervous system during bicuculline induced epilepticus," In: Advances in Neurology vol. 34: Status Epilepticus, (A.V. Delgado–Escueta, C.G. Wasterlain, D.M. Treiman, R.J. Porter, eds), Raven Press, New York, pp 305–310 (1983).

Bazan, N.G. et al., "Membrane lipids in the pathogenesis of brain edema: Phosholipids and arachidonic acid, the earliest membrane components changed at the onset of ischemia," In: Advances in Neurology, vol. 28: Brain Edema. (J. Cervós–Navarro and R. Ferszt, eds), Raven Press, New York, pp 197–205 (1980).

Bazan, N.G. et al., "Membrane–derived lipid second messengers as targets for neuroprotection: Platelet–activating factor," In: Emerging Strategies in Neuroprotection, Advances in Neuroprotection (P.J. Marangos and H. Lal, eds.), Birkhäuser, Boston, pp. 238–251 (1992).

Bazan, N.G. et al., "Platelet–activating factor and other bioactive lipids," In: Cerebrovascular Disease, Pathophysiology, Diagnosis and Management (M.D. Ginsberg and J. Bogousslavsky, eds.) Chapter 37, Blackwell Science Publishers, Malden, Massachusetts, pp. 532–555 (1998).

Bazan, N.G. et al., "Platelet–activating factor is both a modulator of synaptic function and a mediator of cerebral injury and inflammation," In: Advances in Neurology, vol. 71:Cellular and Molecular Mechanisms of Ischemic Brain Damage, (B. Siesjö and T. Wieloch, eds.), Lippincott–Raven Publishers, Philadelphia, vol. 37, pp. 475–484 (1996b).

(List continued on next page.)

Primary Examiner—Robert W. Ramsuer
(74) Attorney, Agent, or Firm—Bonnie J. Davis; John H. Runnels

(57) ABSTRACT

A new series of derivatives of 2,4,6-trimethyl-1,4-dihydropyridine-3,5-dicarboxylic acid and their synthesis have been discovered. Surprisingly, by modifying the substituent of the 3-carboxylic acid group, new compounds were produced with high activity as PAF receptor antagonists. These compounds were shown to protect neurons from brain damage that normally occurs in response to stroke and other cerebrovascular diseases. These compounds are also protective against edema generation resulting from traumatic breakdown of the blood-brain barrier. Moreover, these compounds were found to be non-toxic and cytoprotective of cells undergoing oxidative stress that would normally trigger apoptotic cell death; and to have activity as (a) antagonists of an intracellular platelet activating factor ("PAF")-binding site, (b) inhibitors of PAF- and cytokine-mediated c-aminoterminal jun kinase (JNK) and extracellular regulated kinase (ERK), and (c) transcriptional inhibitors of COX-2 expression.

26 Claims, 12 Drawing Sheets

OTHER PUBLICATIONS

Bazan, N.G. et al., "Regional distribution and rate of production of free fatty acids in rate brain," J. Neurochem., vol. 18, pp. 1387–1393 (1971).

Bennett, S.A.L. et al., "Platelet–activating factor receptor expression is associated with neuronal apoptosis in an in vivo model of excitotoxicity," Cell Death Differentation, vol. 5, pp. 867–875 (1998).

Bito, H. et al., "Platelet–activating factor (PAF) receptor in rat brain: PAF mobilizes intracellular Ca2+ in hippocampal neurons," vol. 9, pp. 285–294 (1992).

Bonavida, B. et al., "Platelet–activating factor and the cytokine network in inflammatory processes," Clin. Rev. Allergy, vol. 12, pp. 381–395 (1994).

Chen, C. et al., "Attenuated long–term potentiation hippocampal dentate gyrus neurons of mice deficient in the platelet–activating factor–receptor," J. Neurophysiol., vol. 85, pp. 384–390 (2001).

Clark, G.D. et al., "Enhancement of hippocampal excitatory synaptic transmission by platelet–activating factor," Neuron, vol. 9, pp. 1211–1216 (1992).

Feurstein., G. et al., "Platelet–activating factor: a putative mediator in central nervous system injury?," Stroke, vol. 21(suppl III), pp. III–90–III–94 (1990).

Gelhard, H.A. et al., "Platelet–activating factor: a candidate human immunodeficiency virus type–1–induced neurotoxin," J. Virol., vol. 68, pp. 4628–4635 (1994).

Honda, Z. et al., "Transfected platelet–activating factor receptor activates mitogen protein (MAP) kinase and MAP kinases kinases in Chinese hamster ovary cells," J. Biol. Chem., vol. 269, pp. 2307–2315 (1994).

Kato, K. et al., "Platelet activating factor as potential retrograde messenger in Ca1 hippocampal long–term potentiation," Nature, vol. 367, pp. 175–179 (1994). Moreover, PAF is a transcriptional activator, and this action is blocked by the intracellular PAF antagonist LAU–8080 (BN–50730).

Kumar, R. et al., "Production and effects of platelet–activating factor in the rat brain," Biochem. Biophys. Acta, vol. 963, pp. 375–383 (1988).

Marcheselli, V. L. et al., "Sustained induction of prostaglandin endoperoxide synthase–2 by seizures in hippocampus: Inhibition by a platelet–activating factor antagonist," J. Biol. Chem., vol. 271, pp. 24794–24799 (1996).

Marcheselli, V.L. et al., "Distinct–platelet–activating factor binding sites in synaptic endings and in intracellular membranes of rat cerebral cortex," J. Biol. Chem., vol. 265, pp. 9140–9145 (1990).

Marcheselli, V.L. et al., "Platelet–activating factor is a messenger in the electroconvulsive shock–induced transcriptional activation of c–fos and zif–268 in hippocampus," J. Neurosci. Res., vol. 37, pp. 54–61, (1994).

Mukherjee, P.K. et al., "Glutamate receptor signaling interplay modulates stress–sensitive mitogen–activated protein kinases and neuronal cell death," J. Biol. Chem., vol. 274, pp. 6493–6498 (1999). Panetta et al., 1987.

Nishida, K. et al., "Platelet–activating factor in brain regions after transient ischemia in gerbils," Stroke, vol. 27, pp. 514–519 (1996).

Panetta, T. et al., "Effects of a platelet–activating factor antagonist (BN 52021) on free fatty acids, dicylglycerols, polyphospho–inositides and blood now in the gerbil brain: Inhibition of ischemia reperfusion induced cerebral injury," Biochem. Biophys. Res. Comm., vol. 149, pp. 580–587 (1987).

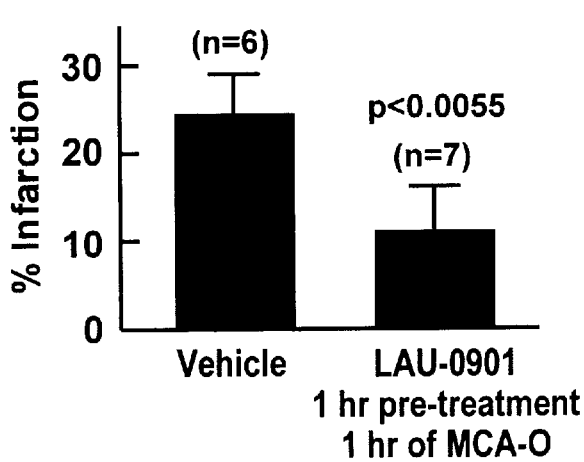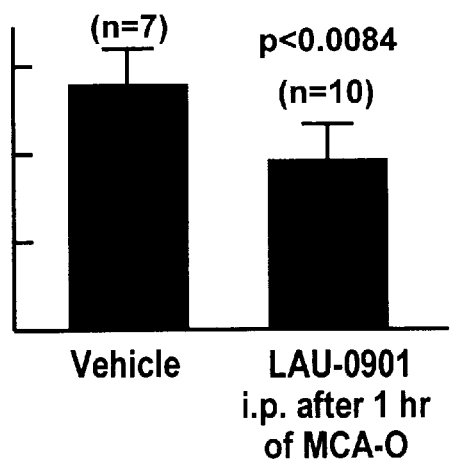
Fig. 12a
Fig. 12b
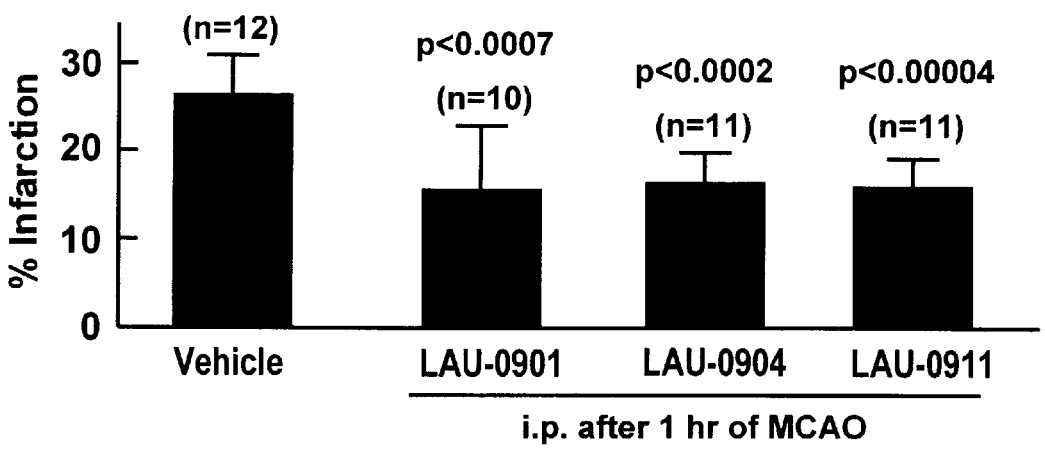
Fig. 12c

2,4,6-TRIMETHYL-1,4-DIHYDRO-PYRIDINE-3,5-DICARBOXYLIC ACID ESTERS AS NEUROPROTECTIVE DRUGS

This invention pertains to a series of new derivatives of 2,4,6-trimethyl-1,4-dihydropyridine-3,5-dicarboxylic acid, their synthesis, and the use of these compounds as platelet-activating factor antagonists, inhibitors of certain protein kinases, transcriptional inhibitors of COX-2 expression, and as agents effective in protecting brain tissue from injuries related to trauma or disease.

Various derivatives of 1,4 dihydropyridines have been described with properties that include one or more of the following: platelet activating factor antagonist activity, coronary vessel dilators, antihypertensives, antiischemic, antithrombotic activity, cerebral vessel dilators, peripheral vessel dilators, renal vessel dilators. See U.S. Pat. Nos. 5,177, 211; 5,070,205; 5,068,337; 4,937,242; 4,801,598; 4,788, 205; 4,755,512; 3,996,234; and 3,974,274. See also, WO 90/12015 and EPO 0325 187.

It has been known for sometime that brain ischemia promotes the accumulation of arachidonic acid. See N. G. Bazan, "Effects of ischemia and electroconvulsive shock on free fatty acid pool in the brain," Biochim. Biophys. Acta, vol. 218, pp. 1–10 (1970); N. G. Bazan, "Changes in free fatty acids of brain by drug induced convulsions, electroshock and anesthesia," J. Neurochem., vol. 18, pp. 1379–1385 (1971). In addition, newborn mammals and adult poikilotherms, unlike adult rodents and nonhuman primates, do not display an arachidonic acid accumulation induced by ischemia. See Bazan 1971; N. G. Bazan et al., "Regional distribution and rate of production of free fatty acids in rat brain," J. Neurochem., vol. 18, pp.1387–1393 (1971); and M. I. Aveldano et al., "Differential lipid deacylation during brain ischemia in a homeotherm and a poikilotherm. Content and composition of free fatty acids and triacylglycerols," Brain Res., vol.100, pp. 99–110 (1975). A connection has been suggested between brain damage and both the accumulation of arachidonic acid and the activation of phospholipase $A_2$, because resistance to brain damage was shown in animals that do not accumulate arachidonic acid (e.g., newborn mammals and mature poikilotherms) but not in animals that accumulate arachidonic acid (e.g., adult mammals). This pattern of resistance to brain damage was shown in animal models subjected to ischemia, stroke, cerebral edema, and epilepsy. See N. G. Bazan et al., "Membrane lipids in the pathogenesis of brain edema: Phospholipids and arachidonic acid, the earliest membrane components changed at the onset of ischemia," In: Advances in Neurology, Vol 28: Brain Edema. (J. Cervós-Navarro and R. Ferszt, eds), Raven Press, New York, pp 197–205 (1980); N. G. Bazan et al., "Endogenous pools of arachidonic acid enriched membrane lipids in cryogenic brain edema," In: Recent Progress in the Study of Brain Edema, (K. G. Go and A. Baethmann, eds), Plenum Press, New York, pp 203–212 (1984); and N. G. Bazan et al., "Free arachidonic acid and membrane lipids in the central nervous system during biculline induced status epilepticus," In: Advances in Neurology Vol 34: Status Epilepticus, (A. V. Delgado-Escueta, C. G. Wasterlain, D. M. Treiman, R. J. Porter, eds), Raven Press, New York, pp 305–310 (1983).

Phospholipase $A_2$ generates the platelet-activating factor ("PAF") precursor as well as arachidonic acid. Platelet-activating factor (PAF) accumulation has been shown to participate in ischemia-reperfusion brain damage and excitotoxic neuronal injury. See N. G. Bazan, "Inflammation: A signal terminator," Nature, vol. 374, pp.501–502 (1995); N. G. Bazan et al., "Platelet-activating factor is both a modulator of synaptic function and a mediator of cerebral injury and inflammation," In: Advances in Neurology, Vol. 71 :Cellular and Molecular Mechanisms of Ischemic Brain Damage, (B. Siesjö and T. Wieloch, eds.), Lippincott-Raven Publishers, Philadelphia, vol. 37, pp. 475–484 (1996b); N. G. Bazan et al., "Platelet-activating factor and other bioactive lipids," In: Cerebrovascular Disease, Pathophysiology, Diagnosis and Management (M. D. Ginsberg and J. Bogousslavsky, eds.) Chapter 37, Blackwell Science Publishers, Malden, Mass., pp. 532–555 (1998); N. G. Bazan et al., "Membrane-derived lipid second messengers as targets for neuroprotection: Platelet-activating factor," In: Emerging Strategies in Neuroprotection, Advances in Neuroprotection (P. J. Marangos and H. Lal, eds.), Birkhäuser, Boston, pp. 238–251 (1992); T. Panetta et al., "Effects of a platelet-activating factor antagonist (BN 52021) on free fatty acids, diacylglycerols, polyphospho-inositides and blood now in the gerbil brain: Inhibition of ischemia reperfusion induced cerebral injury," Biochem. Biophys. Res. Comm., vol.149, pp.580–587 (1987); K. Nishida et al., "Platelet-activating factor in brain regions after transient ischemia in gerbils," Stroke, vol. 27, pp.514–519 (1996); S. A. L. Bennett et al, "Platelet-activating factor receptor expression is associated with neuronal apoptosis in an in vivo model of excitotoxicity," Cell Death Differentiation, vol. 5, pp. 867–875 (1998); H. Bito et al., "Platelet-activating factor (PAF) receptor in rat brain: PAF mobilizes intracellular Ca2+ in hippocampal neurons," Neuron, vol.9, pp. 285–294 (1992); B. Bonavida et al., "Platelet-activating factor and the cytokine network in inflammatory processes," Clin. Rev. Allergy, vol. 12, pp. 381–395 (1994); G. Feurstein et al., "Platelet-activating factor: a putative mediator in central nervous system injury?," Stroke, vol. 21(suppl III), pp. III-90–III-94 (1990); and H. A. Gelbard et al., "Platelet-activating factor: a candidate human immunodeficiency virus type 1-induced neurotoxin," J. Virol., vol. 68, pp. 4628–4635 (1994).

PAF, a potent phospholipid messenger, is released during ischemic insults to the brain and after seizures. See R. Kumar et al., "Production and effects of platelet-activating factor in the rat brain," Biochem. Biophys. Acta, vol. 963, pp.375–383 (1988). Multiple receptors and multiple functions for PAF has been reported. There are seven transmembrane-spanning domain receptors as well as intracellular binding sites for PAF. See Z. Honda et al., "Transfected platelet-activating factor receptor activates mitogen-activated protein (MAP) kinase and MAP kinases kinases in Chinese hamster ovary cells," J. Biol. Chem., vol. 269, pp.2307–2315 (1994); V. L. Marcheselli et al., "Distinct platelet-activating factor binding sites in synaptic endings and in intracellular membranes of rat cerebral cortex," J. Biol. Chem., vol. 265, pp. 9140–9145 (1990); and V. L. Marcheselli et al., "Platelet-activating factor is a messenger in the electroconvulsive shock-induced transcriptional activation of c-fos and zif-268 in hippocampus," J. Neurosci. Res., vol.37, pp. 54–61, (1994). PAF enhances glutamate release at the presynaptic level, which is antagonized by the plasma membrane-type receptor inhibitor BN-52021. See G. D. Clark et al., "Enhancement of hippocampal excitatory synaptic transmission by platelet-activating factor," Neuron, vol.9, pp. 1211–1216 (1992); N. G. Bazan et al., "Platelet activating factor in the modulation of excitatory amino acid neurotransmitter release and of gene expression," J. Lipid Mediat. Cell Signal, vol. 14, pp.321–330 (1996a); and C. Chen et al., "Attenuated long-term potentiation in hippocampal dentate gyrus neurons of mice deficient in the platelet-activating factor receptor," J. Neurophysiol., vol. 85, pp. 384–390 (2001).

PAF is also a retrograde messenger of long-term synaptic potentiation. See K. Kato et al., "Platelet activating factor as a potential retrograde messenger in Ca1 hippocampal long-term potentiation," Nature, vol. 367, pp. 175–179 (1994). Moreover, PAF is a transcriptional activator, and this action is blocked by the intracellular PAF antagonist LAU-8080 (BN-50730). See V. L. Marcheselli et al., 1994; V. L. Marcheselli et al., "Sustained induction of prostaglandin endoperoxide synthase-2 by seizures in hippocampus: Inhibition by a platelet-activating factor antagonist," J. Biol. Chem., vol. 271, pp. 24794–24799 (1996); Bazan et al., "Platelet-activating factor and retinoic acid synergistically activate the inducible prostaglandin synthase gene," Proc. Natl. Acad. Sci., vol. 91, pp. 5252–5256 (1994); P. K. Mukherjee et al., "Glutamate receptor signaling interplay modulates stress-sensitive mitogen-activated protein kinases and neuronal cell death," J. Biol. Chem., vol.274, pp. 6493–6498 (1999).

Membrane-type PAF receptor antagonists exert dose-dependent protective effects in brain ischemia/reperfusion animal models. See Panetta et al., 1987; Nishida et al., 1996. The bioactive lipid PAF is a key modulator in glutamate signaling. Bazan et al., 1996a, b). The signaling of glutamate initiates a critical pathway during stroke that leads to activation of specific phospholipases $A_2$, which in turn leads to more PAF production and activation of stress-sensitive protein kinases. This in turn leads to activation and translocation of transcription factors and hypoxia-inducible factors, followed by gene expression activation, in particular of the cyclooxygenase-2 (COX-2) gene. See Bazan et al., 1994; Marcheselli et al, 1994; and Marcheselli et al, 1996.

We have discovered a series of novel derivatives of 2,4,6-trimethyl-1,4-dihydropyridine-3,5-dicarboxylic acid (hereinafter, called the "LAU-0900 series compounds" and each compound given an unique LAU-0900 number) and a novel synthesis of the derivatives. Surprisingly, by modifying the substituent of the 3-carboxylic acid group, new compounds were produced with higher activity as PAF receptor antagonists than commercially available PAF antagonists, e.g., WEB 2086BS, CV-6209, CV-3988, and the Ginkolide-B (BN-52021). In particular, these new compounds displayed a higher specificity for the intracellular binding site, and the duration of their effect was longer. These compounds were shown to protect neurons from brain damage that occurs in response to stroke and other cerebrovascular diseases, as ascertained both in a curative experimental design in a mouse model of stroke and in a preventive experimental design. These compounds are also effective in protecting damage caused by traumatic head injury and vasogenic edema. Moreover, these compounds were found to be nontoxic and cytoprotective of cells undergoing oxidative stress that would normally trigger apoptotic cell death; and to have activity as (a) antagonists of an intracellular platelet activating factor ("PAF")-binding site, (b) inhibitors of PAF- and cytokine-mediated c-aminoterminal jun kinase (JNK) and extracellular regulated kinase (ERK), and (c) transcriptional inhibitors of COX-2 expression. It is believed that these compounds would be neuroprotective in other neural injuries, including spinal cord injury, status epilepticus-induced brain injury, traumatic head injury, neurodegenerative diseases (e.g., Alzheimer's disease), ischemia-reperfusion injury to other organs (e.g., heart or kidney), ischemic retinal diseases, retinal degenerative diseases, and vasogenic injuries.

BRIEF DESCRIPTION OF THE DRAWINGS

FIG. 12a illustrates the decrease in the infarction volume (neuroprotective activity) obtained in mice when LAU-0901 (30 mg/kg) was injected 1 hr prior to middle cerebral artery occlusion (MCA-O) for 1 hr, and the mice killed for brain analysis 24 hr after reperfusion.

FIG. 12b illustrates the decrease in the infarction volume (neuroprotective activity) obtained in mice when LAU-0901 (30 mg/kg) was injected at the onset of middle cerebral artery occlusion (MCA-O) for 1 hr, and the mice killed for brain analysis 24 hr after reperfusion.

FIG. 12c illustrates the decrease in the infarction volume (neuroprotective activity) obtained in mice when either LAU-0901, LAU-0904, or LAU-0911 (30 mg/kg) was injected 1 hr after reperfusion following middle cerebral artery occlusion (MCA-O) for 1 hr, and the mice killed for brain analysis 48 hr after reperfusion.

Figure 1:
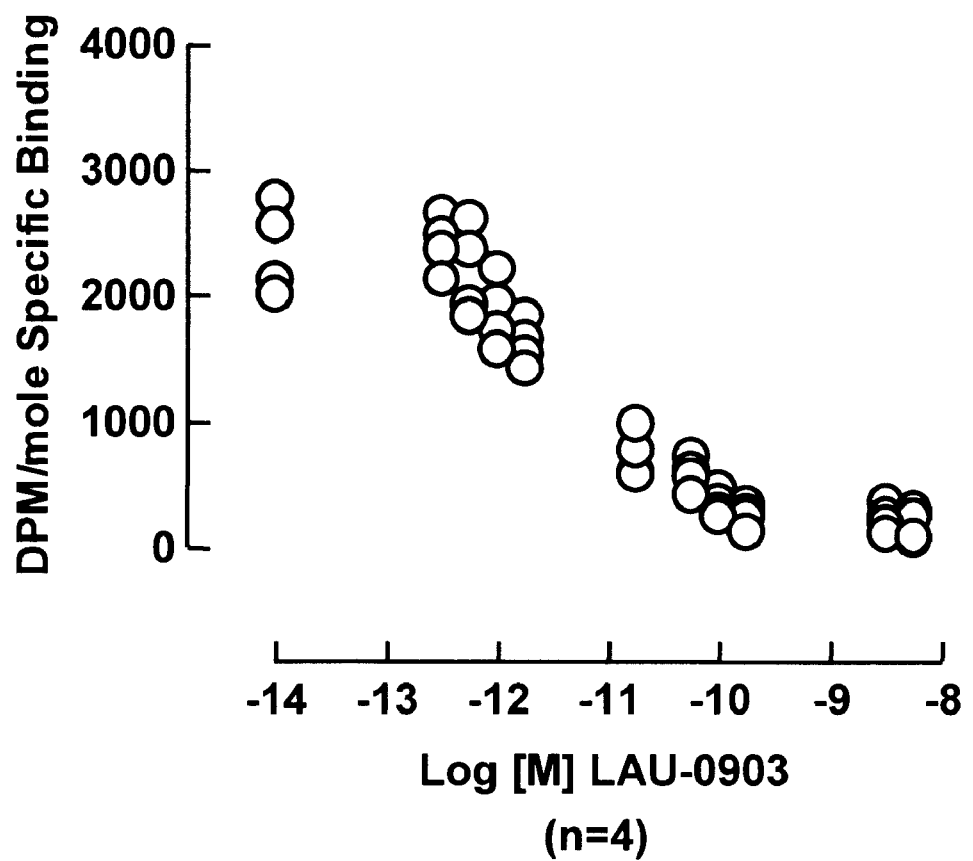
FIG. 1 illustrates the competition by LAU-0903 for $^3$H-PAF (platelet-activating factor) binding to microsomal membranes isolated from rat brain cortex.

The present invention is a new series of 4-methyl-1,4-dihydropyridine-3,5-dicarboxylic acid derivatives, of general formula I as shown below, having activity as PAF receptor antagonists, the pharmaceutical compositions containing these compounds and the methods of preparation.

General Formula I

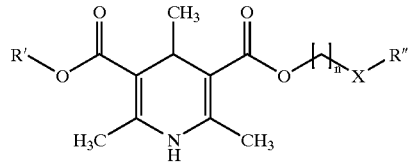

The products of the invention have the general formula I ("LAU 0900" series compounds), where:

R' is a methyl group or 1,3-di-(4-morpholinyl)-2-propyl;
R" is 3,4-dichlorophenyl; 4-fluorophenyl; 4-imidazol-1-phenyl; 4-propoxyphenyl; 4-butoxyphenyl; 4-(3-oxo-buten-1-yl)phenyl; 3,4,5-trimethoxyphenyl; 4-butyryl phenyl; or 4-methoxyiminomethylphenyl;
n is either 2 or 3; and
X defines an atom of oxygen (O) or sulfur (S).

The pharmacological activity of compounds of formula I has been determined as indicated below in Examples 15 through 22. Pharmaceutically acceptable acid addition salts of the compounds of General Formula I are those formed from acids which form non-toxic acid addition salts, for example, the hydrochloride, hydrobromide, sulphate or bisulphate, phosphate or acid phosphate, succinate, tartrate, methanesulfphonate and benzenesulphonate.

The compounds of General Formula I may be obtained according to the following reaction scheme:

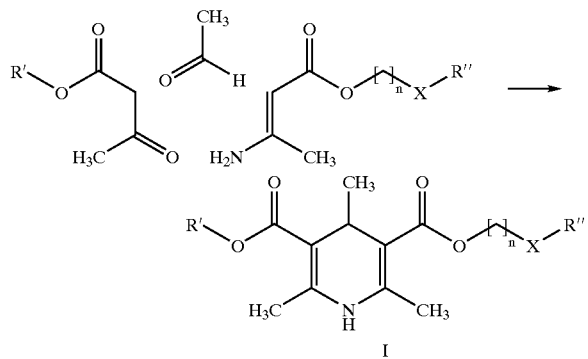

where R', R", n and X are as described above. The starting materials are either known compounds or can be synthesized by methods known to a person skilled in the art.

The compounds of General Formula I can be used as medication to be administered orally, rectally, topically, parenterally or inhalation, in the form of a pharmaceutical preparation, which contains at least one of the compounds of General Formula I in combination with a pharmaceutically acceptable carrier. The pharmaceutical carrier is selected with regard to the intended route of administration and standard pharmaceutical practice. For example, the compounds may be administered orally in the form of tablets containing such excipients as starch or lactose, or in capsules or ovules either alone or in admixture with excipients, or in the form of elixirs or suspensions containing flavoring or coloring agents. They may be injected parenterally, for example, intravenously, intramuscularly, or subcutaneously. For parenteral administration, they are best used in the form of a sterile aqueous solution which may contain other substances, for example, salts or glucose. The amount of active compound is between 0.1 and 99% by weight of the preparation, preferably between 2 and 50% by weight in oral preparations. The daily dose of the active substance depends on the type of administration and, in general, is between 25 and 100 mg if administered orally and between 0.1 and 50 mg per dose if administered intravenously. In clinical practice, the dosage will be adjusted for the particular patient and may vary with age, weight, and response of the patient. The above dosages are exemplary of an average case but can be increased or lowered if merited.

The preparation of the compounds of General Formula I is further illustrated by the following examples. All the starting materials were of commercial origin. Both acetoacetates and aminocrotonates were prepared according to commonly known procedures in relation with the Hantzsch synthesis of 1,4-dihydropyridines. See J. A. Joule and K. Mills, "Heterocyclic Chemistry," 4$^{th}$ Edition, Blackwell Science, Boston, Mass. (2000).

EXAMPLE 1

Synthesis of 2,4,6-Trimethyl-1,4-dihydro-pyridine-3,5-dicarboxylic acid 5-[2-(3,4-dichloro phenoxy)] ethyl ester 3-[1,3-di-(4-morpholinyl)-2-propyl-1-ester dihydrochloride (LAU-0901)

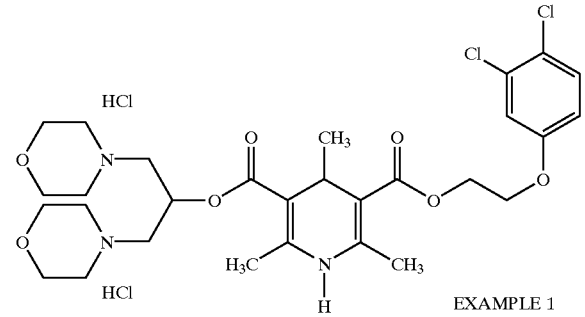

In a 25 mL flask, with stirring and in the absence of light, 0.94 g (3 mmol) of 3-amino-2-butenoic acid 2-morpholin-4-yl-1-morpholin-4-ylmethyl-ethyl ester, 0.87 g (3 mmol) of 3-oxo-butyric acid 2-(3,4-dichloro-phenoxy)-ethyl ester, and 0.2 g (4.5 mmol) of acetaldehyde were dissolved in 5 mL of dry methanol. The mixture was then refluxed for 8 hr under a nitrogen atmosphere. The solvent was removed by evaporation to dryness at room temperature. The remaining oil was dissolved in 40 mL of ethyl ether and 5 mL of a saturated solution of HCl, and ethyl ether (Et$_2$O) was added dropwise with vigorous stirring. The formed precipitate was filtered, washed with 10 mL of dry Et$_2$O and dried at 40° C. with vacuum, yielding 2.02 g (98% yield) of a yellow solid: Mp=155–158° C. (dry acetone); IR (KBr) $\nu_{max}$ 3272, 3077, 2960, 1693, 1671, 1481, 1455, 1298, 1214, 1135, 982, 774 cm$^{-1}$; $^1$H NMR (CDCl$_3$) $\delta$9.07 (s, 1H), 7.53 (d,J=8.86 Hz, 1 H), 7.28 (d,J=2.82 Hz,IH), 6.98 (dd,J$_1$=8.86 Hz,J$_2$=2.82

Hz, 1H), 5.56 (s, 1H), 4.43–4.22 (m, 4H), 4.10–3.70 (m, 8H), 3.68–2.98 (m, 14H), 2.25 (s, 3H), 2.20 (s, 3H), 0.98 (d, J=6.44 Hz, 3H).

Quantitative Analysis: Calculated for $C_{29}H_{41}N_3O_7Cl_4$

|  | % C | % H | % N |
|---|---|---|---|
| Calculated: | 50.81 | 6.03 | 6.13 |
| Found: | 50.55 | 6.30 | 5.82 |

EXAMPLE 2

Synthesis of 2,4,6-Trimethyl-1,4-dihydro-pyridine-3,5-dicarboxylic acid 5-[3-(4-fluorophenysulfanyl)]-propyl-1-ester 3-methyl ester (LAU-0904)

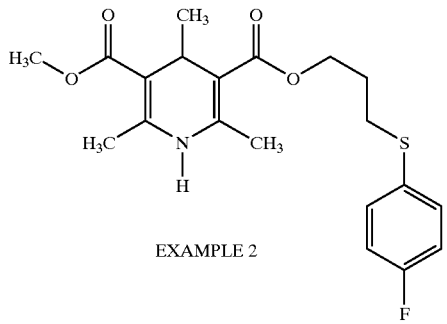

EXAMPLE 2

In a 25 mL flask, with stirring and in the absence of light, 1.34 g (5 mmol) of 3-amino-2-butenoic acid 3-(4-fluoro-phenylsulfanyl)-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was then cooled to −10° C. overnight. The formed precipitate was filtered and washed with 3 mL of cold EtOH, yielding 1.34 g (73%) of a white crystalline compound: Mp=86–88° C. (diisopropyl ether); IR (KBr)$\nu_{max}$ 3344, 2944, 1698, 1640, 1491, 1223, 1140, 1053, 839, 778 cm$^{-1}$; $^1$H NMR (CDCl$_3$) δ7.38–7.31 (m, 2H), 6.98 (t, J=8.13 Hz, 2H), 5.55 (s, 1H), 4.30–4.10(m, 2H), 3.79 (q, J=6.34 Hz, 1H), 3.71 (s, 3H), 2.95 (t, J=7.27 Hz, 2H), 2.26 (s, 3H), 2.25 (s, 3H), 2.10–1.90 (m, 2H), 0.94 (d, J=6.34 Hz, 3H).

Quantitative Analysis. Calculated for $C_{20}H_{24}NO_5F$

|  | % C | % H | % N |
|---|---|---|---|
| Calculated: | 63.65 | 6.41 | 3.71 |
| Found: | 63.35 | 6.56 | 3.82 |

EXAMPLE 3

Synthesis of 2,4,6-Trimethyl-1,4-dihydro-pyridine-3,5-dicarboxylic acid 5-[3-(4-imidazol-1-yl-phenoxy)]-propyl-1-ester 3-methyl ester (LAU-0902)

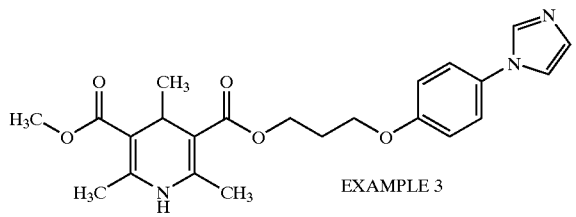

EXAMPLE 3

In a 25 mL flask, with stirring and in the absence of light, 1.43 g (5 mmol) of 3-amino-2-butenoic acid 3-(4-imidazol-1-yl-phenoxy)-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.1 g (50%) of a white crystalline compound: Mp=115–7° C. (EtOH).

Quantitative Analysis. Calculated for $C_{23}H_{27}N_3O_5$

|  | % C | % H | % N |
|---|---|---|---|
| Calculated: | 64.93 | 6.40 | 9.88 |
| Found: | 64.75 | 6.56 | 9.92 |

EXAMPLE 4

Synthesis of 2,4,6-Trimethyl-1,4-dihydro-pyridine-3,5-dicarboxylic acid 5-[3-(imidazol-1-yl-phenylsulphanyl)]-propyl-1-ester 3-methyl ester (LAU-0903)

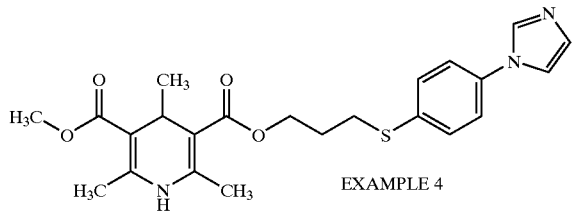

EXAMPLE 4

In a 25 mL flask, with stirring and in the absence of light, 1.51 g (5 mmol) of 3-amino-2-butenoic acid 3-(4-imidazol-1-yl-phenylsulfanyl)-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.34 g (6 1%) of a white crystalline compound: Mp=116–118° C. (EtOH).

Quantitative Analysis. Calculated for $C_{23}H_{27}N_3O_4S$

|  | % C | % H | % N |
|---|---|---|---|
| Calculated: | 62.56 | 6.16 | 9.52 |
| Found: | 62.42 | 6.38 | 9.68 |

EXAMPLE 5

Synthesis of 2,4,6-Trimethyl-1,4-dihydro-pyridine-3,5-dicarboxylic acid 5-[3-(4-butoxyphenylsulfanyl)]-propyl-1-ester 3-methyl ester (LAU-0905)

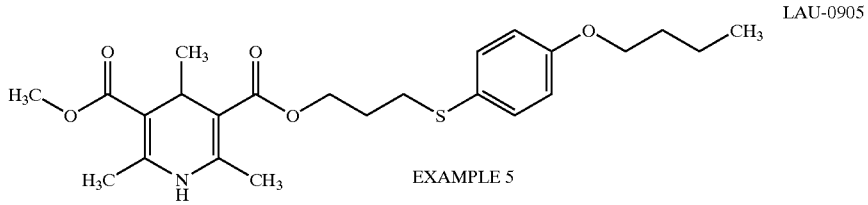

EXAMPLE 5

In a 25 mL flask, with stirring and in the absence of light, 1.61 g (5 mmol) of 3-amino-2-butenoic acid 3-(4-butoxyphenylsulfanyl)-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.25 g (56%) of a white crystalline compound: Mp=55–57° C. (diisopropyl ether).

Quantitative Analysis. Calculated for $C_{24}H_{33}NO_5S$

|  | % C | % H | % N |
|---|---|---|---|
| Calculated: | 64.40 | 7.43 | 3.13 |
| Found: | 64.32 | 7.66 | 3.28 |

EXAMPLE 6

Synthesis of 2,4,6-Trimethyl-1,4-dihydro-pyridine-3,5-dicarboxylic acid 5-[3-(4-propoxyphenylsulfanyl)]-propyl-1-ester 3-methyl ester (LAU-0907)

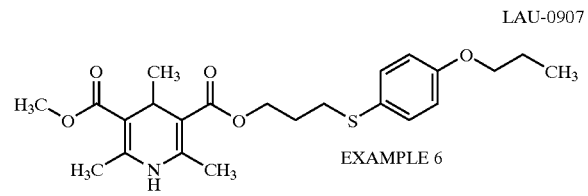

EXAMPLE 6

In a 25 mL flask, with stirring and in the absence of light, 1.54 g (5 mmol) of 3-amino-2-butenoic acid 3-(4-propoxyphenylsulfanyl)-propyl ester, 0.58 g (5 mmol) of acetyl acetate methyl ester, and 0.3 g (6.8 mmol) of acetaldehyde, were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.41 g (65%) of a white crystalline compound: Mp=60–2° C. (diisopropyl ether).

Quantitative Analysis. Calculated for $C_{23}H_{31}NO_5S$

|  | % C | % H | % N |
|---|---|---|---|
| Calculated: | 63.72 | 7.21 | 3.23 |
| Found: | 63.81 | 7.35 | 3.28 |

EXAMPLE 7

Synthesis of 2,4,6-Trimetityl-1,4-dihydropyridine-3,5-dicarboxylic acid 3-[3-(4-propoxy-phenoxy)propyl]ester 5-methyl ester (LAU-0909)

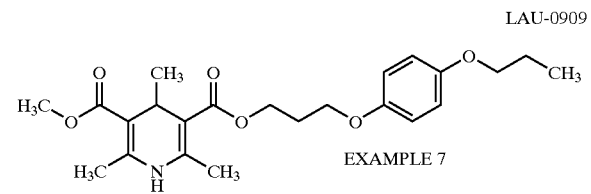

EXAMPLE 7

In a 50 mL flask, with stirring and in the absence of light, 4.40 g (15 mmol) of 3-amino-2-butenoic acid 3-(4-propoxy-phenoxy)-propyl ester, 1.27 mL (22.5 mmol) of acetaldehyde, and 1.78 mL (16.5 mmol) of methyl acetoacetate were dissolved in 10 mL of absolute ethanol. A nitrogen stream was passed through the system while the mixture was refluxed for 8 hr. The solvent was removed to dryness, and the crude was submitted to column chromatography over silica gel, using hexane-diethyl ether (1:1) as an eluent. The effluent solution was concentrated to dryness, yielding 5.0 g (80%) of a white solid. Mp=126–127° C. (hexane-diethyl ether);

Quantitative Analysis. Calculated for $C_{23}H_{31}NO_6$

|  | % C | % H | % N |
|---|---|---|---|
| Calculated: | 66.17 | 7.48 | 3.35 |
| Found: | 66.35 | 7.29 | 3.22 |

EXAMPLE 8

Synthesis of 2,4,6-Trimethyl-1,4-dihydropyridine-3,5-dicarboxylic acid 3-[3-(4-butoxyphenoxy)propyl] ester 5-methyl ester (LAU-0910)

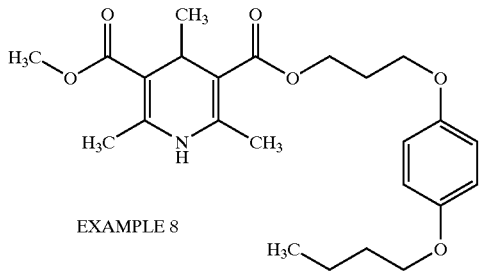

EXAMPLE 8

In a 50 mL flask, with stirring and in the absence of light, 4.61 g (15 mmol) of 3-amino-2-butenoic acid 3-(4-butoxy-phenoxy)-propyl ester, 1.27 mL (22.5 mmol) of acetaldehyde, and 1.78 mL (16.5 mmol) of methyl acetoacetate were dissolved in 10 mL of absolute ethanol. A nitrogen stream was passed through the system while the mixture was refluxed for 8 hr. The solvent was removed to dryness, and the crude was submitted to column chromatography over silica gel, using hexane-diethyl ether (1:1) as an eluent. The effluent solution was concentrated to dryness, yielding 5.65 g (87%) of a white solid. Mp=93–94° C. (hexane-diethyl ether); IR (KBr)$v_{max}$ 3340, 2958, 1697, 1650, 1509, 1490, 1299, 1221, 1139, 1060, 826 cm$^{-1}$; $^1$H NMR (CDCl$_3$) δ6.81 (s, 4H); 5.62 (bs, 1H); 3.32–4.24 (m, 2H); 4.02 (t, 2H, J=6.22 Hz); 3.91–3.80 (m, 3H); 3.69 (s, 3H); 2.26 (s, 3H); 2.25 (s, 3H); 2.13 (q, 2H, J=6.22 Hz); 1.73 (q, 2H, J=6.59 Hz); 1.49 (c, 2H,J=7.32 Hz); 0.98–0.93 (m, 6H)ppm.

Quantitative Analysis. Calculated for $C_{24}H_{32}NO_6$

|  | % C | % H | % N |
|---|---|---|---|
| Calculated: | 66.80 | 7.71 | 3.25 |
| Found: | 66.77 | 7.79 | 2.92 |

EXAMPLE 9

Synthesis of 2,4,6-Trimethyl-1,4dihydro-pyridine-3,5-dicarboxylic acid 5-[4-3oxo-but-1-enyl)-phenoxy]-propyl-1-ester 3-methyl ester (LAU-0908)

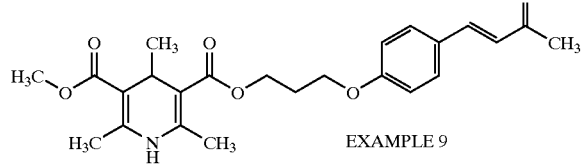

EXAMPLE 9

In a 25 mL flask, with stirring and in the absence of light, 1.51 g (5 mmol) of 3-amino-2-butenoic acid 3-{4-(3-oxo-1-butenyl)-phenoxy]-propyl ester, 0.58 g (5 mmol) of acetyl acetate methyl ester, and 0.3 g (68 mmol) of acetaldehyde were dissolved in 5 mL of absolute ethanol. The mixture was then refluxed for 8 hr under a nitrogen atmosphere. Once the mixture reached room temperature, it was cooled at –10° C. overnight. The formed precipitate was filtered and washed with 3 mL of cold EtOH, yielding 1.11 g (52%) of a white crystalline compound. Mp=120–2° C. (EtOH).

Quantitative Analysis. Calculated for $C_{24}H_{29}NO_6$

|  | % C | % H | % N |
|---|---|---|---|
| Calculated: | 67.43 | 6.84 | 3.28 |
| Found: | 67.21 | 7.02 | 3.45 |

EXAMPLE 10

Synthesis of 2,4,6-Trimethyl-1,4-dihydro-pyridine-3,5-dicarboxylic acid 5-(3,4,5-trimethoxyphenoxy)-propyl-1-ester 3-methyl ester (LAU-0911)

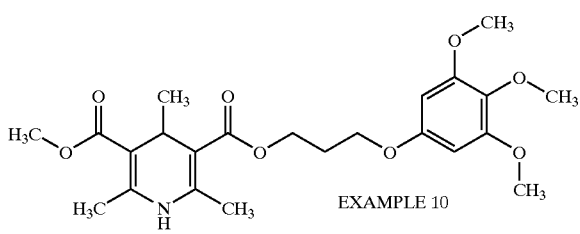

EXAMPLE 10

In a 25 mL flask, with stirring and in the absence of light, 1.62 g (5 mmol) of 3-amino-2-butenoic acid 3-(3,4,5-trimethoxy-phenoxy)-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at –10° C. overnight. The formed precipitate was filtered and washed with 3 mL of cold EtOH, yielding 1.48 g (66%) of a white crystalline compound: Mp=75–7° C. (diisopropyl ether).

Quantitative Analysis. Calculated for $C_{23}H_{31}NO_8$

|  | % C | % H | % N |
|---|---|---|---|
| Calculated: | 61.46 | 6.95 | 3.12 |
| Found: | 61.21 | 6.76 | 3.34 |

EXAMPLE 11

Synthesis of 2,4,6-Trimethyl-1,4-dihydropyridine-3,5dicarboxylic acid 3-methyl ester 5-[3-(3,4,5-trimethoxyphenylsulfanyl)propyl]ester (LAU-0912)

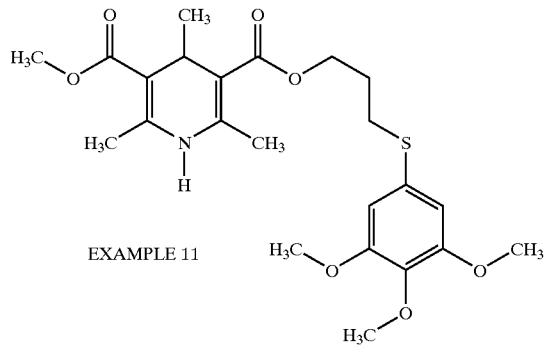

EXAMPLE 11

In a 50 mL flask, with stirring and in the absence of light, 1.79 g (5.24 mmol) of 3-Amino-2-butenoic acid 3-(3,4,5-trimethoxyphenylsulfanyl)propyl ester, 0.346 g (7.86 mmol) of acetaldehyde, and 0.62 mL (5.76 mmol) of methyl acetoacetate were dissolved in 8 mL of absolute ethanol. A nitrogen stream was passed through the system while the mixture was refluxed for 12 hr. The solvent was removed to dryness, and the crude was submitted to column chromatography over silica gel, using hexane-tBuMe ether (1:1) as an eluent. The effluent solution was concentrated to dryness, yielding 0.97 g (40%) of a white solid. Mp=73–75° C. (diisopropyl ether); IR (KBr)$\nu_{max}$ 3356, 3097, 1689, 1580, 1498, 1300, 1217, 1126, 1092, 1058 cm$^{-1}$; $^1$H NMR (CDCl$_3$) δ.6.62(s, 2H); 5.54 (s, 1H), 4.29–4.20 (m, 2H); 3.90–3.76 (m, 10 H); 3.70 (s, 3H); 2.98 (t, 2H, J=7.3 Hz); 2.26 (s, 3H); 2.25 (s, 3H); 2.00 (q, 2H, J=7.3 Hz); 0.95 (d, 3H, J=6.6 Hz).

Quantitative Analysis. Calculated for $C_{23}H_{30}NO_7S$

|  | % C | % H | % N |
|---|---|---|---|
| Calculated: | 59.34 | 6.71 | 3.01 |
| Found: | 59.07 | 6.79 | 2.70 |

EXAMPLE 12

Synthesis of 2,4,6-Trimethyl-1,4-dihydro-pyridine-3,5-dicarboxylic acid 5-[3-(4-butyryl-phenoxy)-propyl]1-ester 3-methyl ester (LAU-0913)

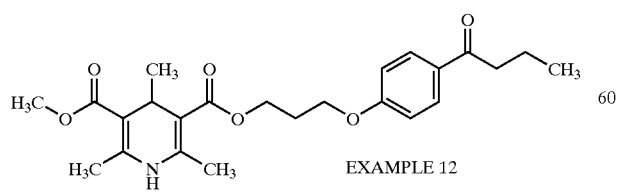

EXAMPLE 12

In a 25 mL flask, with stirring and in the absence of light, 1.52 g (5 mmol) of 3-amino-2-butenoic acid 3-[3-(4-butyryl-phenoxy)-propyl]ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.37 g (64%) of a white crystalline compound: Mp 107–109° C. (EtOH).

Quantitative Analysis. Calculated for $C_{24}H_{31}NO_6$

|  | % C | % H | % N |
|---|---|---|---|
| Calculated: | 67.11 | 7.27 | 3.26 |
| Found: | 67.34 | 7.09 | 3.34 |

EXAMPLE 13

Synthesis of 2,4,6-Trimethyl-1,4-dihydro-pyridine-3,5-dicarboxylic acid 5-[13-(4-butyryl-phenoxy)-propyl]1-ester 3-methyl ester (LAU-0906)

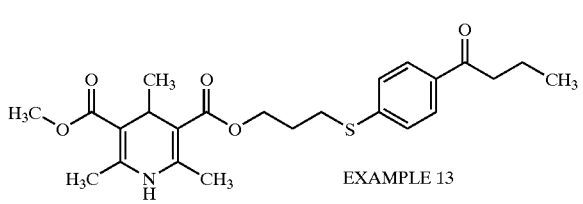

EXAMPLE 13

In a 25 mL flask, with stirring and in the absence of light, 1.61 g (5 mmol) of 3-amino-2-butenoic acid 3-[3-(4-butyryl-phenoxy)-propyl]ester, 0.58 g (5 mmol) of acetylacetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, affording 1.34 g (60%) of a white crystalline compound: Mp 93–95° C. (EtOH).

Quantitative Analysis. Calculated for $C_{24}H_{31}NO_6$

|  | % C | % H | % N |
|---|---|---|---|
| Calculated: | 67.11 | 7.27 | 3.26 |
| Found: | 67.34 | 7.09 | 3.34 |

EXAMPLE 14

Synthesis of 2,4,6-Trimethyl-1,4-dihydro-pyridine-3,5-dicarboxylic acid 3-{3-[4-(methoxylmino-methyl)-phenoxy]-propyl}ester 5-methyl ester (LAU-0914)

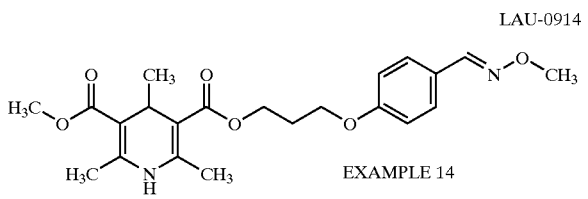

EXAMPLE 14

In a 25 mL flask, with stirring and in the absence of light, 1.46 g (5 mmol) of 3-amino-2-butenoic acid 3-[4-(methoxyimino-methyl)-phenoxy]-propyl ester, 0.58 g (5 mmol) of acetyl acetate methyl ester, and 0.3 g (6.8 mmol) of acetaldehyde were dissolved in 5 mL of absolute ethanol. The mixture was then refluxed for 8 hr under a nitrogen atmosphere. Once the mixture reached room temperature, it was cooled at −10° C. overnight. The formed precipitate was filtered and washed with 3 mL of cold EtOH, yielding 1.31 g (63%) of a white crystalline compound. Mp 93–4° C. (EtOH).

Quantitative Analysis. Calculated for $C_{22}H_{25}N_2O_6$

|  | % C | % H | % N |
|---|---|---|---|
| Calculated: | 63.45 | 6.78 | 6.73 |
| Found: | 63.24 | 76.69 | 6.96 |

The above compounds were used in the following experiments to assess their activity as (a) antagonists of an intracellular platelet activating factor ("PAF")-binding site, (b) inhibitors of PAF- and cytokine-mediated c-aminoterminal jun kinase (JNK) and extracellular regulated kinase (ERK), (c) transcriptional inhibitors of COX-2 expression platelet-activating factor receptor antagonists, and (d) neuroprotectors.

EXAMPLE 15

LAU-0900 Series Are Intracellular Platelet-Activating Factor Receptor Antagonists To test LAU-0900 series antagonistic activity on the binding of $^3$H-platelet-activating factor ($^3$H-PAF) to receptors, competitive and displacement curves were run on rat brain microsomal preparations to assess for the intracellular type receptor (high-affinity binding site with $K_d$: $2.503 \times 10^{-12}$ M, and low-affinity binding site, $K_d$: $30 \times 10^{-9}$ M), or on homogenates of CHO-B cells which over-express the cell-surface-type PAF receptor (a single low-affinity binding site with a $K_d$: $1.505 \times 10^{-10}$ M).

Binding studies were performed on subcellular fractions of tissues obtained from rat brain cortex, according to procedures described in V. Marcheselli et al., "Distinct platelet-activating factor binding sites in synaptic endings and in intracellular membranes of rat cerebral cortex," J. biol. Chem., vol. 265, pp. 9140–9145 (1990). Freshly dissected brain tissues were homogenized in ice-cold buffer (50 mM Tris-HCl, 2 mM EGTA, 5 mM PMSF, 250 mM sucrose, 7.4 pH). Subcellular fractions were obtained by differential centrifugation. The microsomal fraction was sedimented after 100,000×g for 1 hour centrifugation. In addition, three cell lines from Chinese hamster ovary (CHO) with varying expression of PAF receptors, CHO-A, CHO-B, and CHO-C cells (from Dr. Takao Shiizu, University of Tokyo, Tokyo, Japan) were cultured to the fourth-passage cells. These cells were cultured to confluence, then detached from their culturing flasks, and pelleted by rapid centrifugation (3,000 rpm, 10 min). Cellular pellets were homogenized in ice-cold buffer as described above. Freshly obtained microsomal fractions or CHO cellular homogenates were utilized for saturation, displacement, and competition studies using $^3$H-PAF as the hot ligand, unlabeled-PAF to detect non-specific binding, and a LAU-0900 series compound to displace by competition $^3$H-PAF bound to a receptor.

Table 1 shows the effects of competitive displacement experiments using LAU-0903 as a competition for PAF binding. Table 1 shows the PAF receptor dissociation constants ($K_d$) in rat brain microsomal fraction, as well as in homogenates of CHO-B (a cell line with a high expression of PAF receptors) CHO-A (a cell line with a mild expression of PAF receptor) and CHO-C (a cell line that does not express PAF receptors). See B. Liu et al., "Implication of protein kinase C alpha in PAF-stimulated phospholipase D Activation in Chinese hamster ovary (CHO) cells expressing PAF receptor," Biochem. Biophys. Res. Commun., vol.214, pp.418–423 (1995). Table 1 indicates that LAU-0903 was an effective competitor for receptos in both the microsomal fraction and CHO-B cell homogenates. Both the constants of inhibition (KI) and 50% of inhibitory activity ($IC_{50}$) were significant at a low concentration of LAU-0903. This indicates that LAU-0903 is a strong inhibitor for high- and low-affinity PAF-binding sites.

TABLE 1

Competitive Displacement of of $^3$H-PAF from Membrane Preparations by LAU-0903

| Membrane prep source | $K_d$ $^3$H-PAF (M) | LAU-0903 $IC_{50}$ (M) | LAU-0903 KI (M) |
|---|---|---|---|
| Rat brain microsomal | H: $2.053 \times 10^{-12}$<br>L: $30 \times 10^{-9}$ | H: $1.068 \times 10^{-12}$<br>L: $1.439 \times 10^{-10}$ | $1.222 \times 10^{-13}$ |
| CHO-B (heavily overex PAF-R) | $1.505 \times 10^{-10}$ | $5.379 \times 10^{-11}$ | $1.920 \times 10^{-14}$ |
| CHO-A (moderately exp PAF-R) | $1.676 \times 10^{-4}$ | No displacement | No displacement |
| CHO-C (do not exp PAF-R) | No binding | No displacement | No displacement |

Table 2 shows the results of the experiments to assess the comparative displacement of $^3$H-PAF by several of the LAU-0900 series compounds from the high affinity binding receptor of the rat microsomal receptors. Table 2 shows that all compounds tested were effective, but that the greatest displacement was shown by LAU-0901, followed by LAU-0903, LAU-0907, and LAU-0911.

TABLE 2

Comparative $^3$H-PAF Displacement by Novel LAU-0900 Series PAF Antagonists from Microsomal Membranes from Rat Brain

| Compound | $IC_{50}$ |
|---|---|
| LAU-0901 | $3.13 \times 10^{-13}$ |
| LAU-0903 | $1.068 \times 10^{-12}$ |
| LAU-0904 | $1.76 \times 10^{-10}$ |
| LAU-0905 | $1.56 \times 10^{-10}$ |

TABLE 2-continued

Comparative $^3$H-PAF Displacement by Novel LAU-0900 Series
PAF Antagonists from Microsomal Membranes from Rat Brain

| Compound | IC$_{50}$ |
|---|---|
| LAU-0907 | 1.06 × 10$^{-12}$ |
| LAU-0911 | 1.02 × 10$^{-12}$ |

Figure 2:
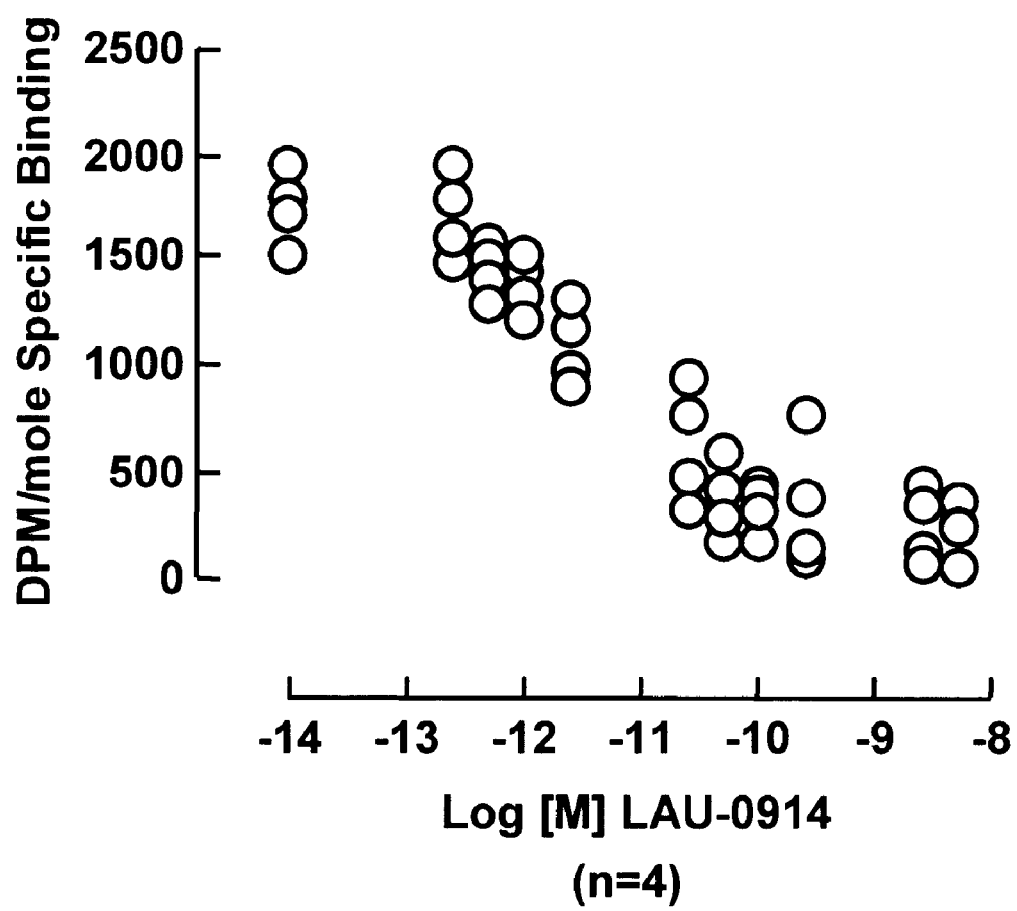
FIG. 2 illustrates the competition by LAU-0914 for $^3$H-PAF (platelet-activating factor) binding to microsomal membranes isolated from rat brain cortex.

FIGS. 1 and 2 show competition by LAU-0903 and LAU-0914 in $^3$H-PAF binding to the rat brain cortex microsomal receptor. FIG. 1 is a graph of the results obtained with LAU-0903. The rat brain microsomal preparation showed a characteristic two-step sigmoidal binding curve, indicating that the antagonist LAU-0903 had competitive activity at both binding sites for $^3$H-PAF. The displacement by LAU-0903 was significant (p<0.02), with an IC$_{50}$: 1.068×10$^{-12}$ M for the high-affinity binding site, and an IC$_{50}$: 1.439×10$^{-10}$ M for the low-affinity binding site.

FIG. 2 illustrates the results of competitive studies of LAU-0914 displacement of binding activity by $^3$H-PAF in microsomal membrane preparation from rat brain cortex. In this experiment, the binding pattern in the rat brain microsomes showed only a single-step sigmoidal curve, indicating that the antagonist LAU-0914 displayed competitve activity at the high-affinity binding site only. Statistical analysis of four experiments indicated that the displacement by LAU-0914 was significant (p<0.0014), with an IC$_{50}$: 2.94068×10$^{-12}$ M for the high-affinity binding site.

FIGS. 1 and 2 illustrate that LAU-0903 and LAU-0914 have different competitive profiles. LAU-0903 showed a double-step sigmoidal curve, indicating two binding-site displacements, while LAU-0914 showed activity only at the high-affinity binding site.

Figure 3:
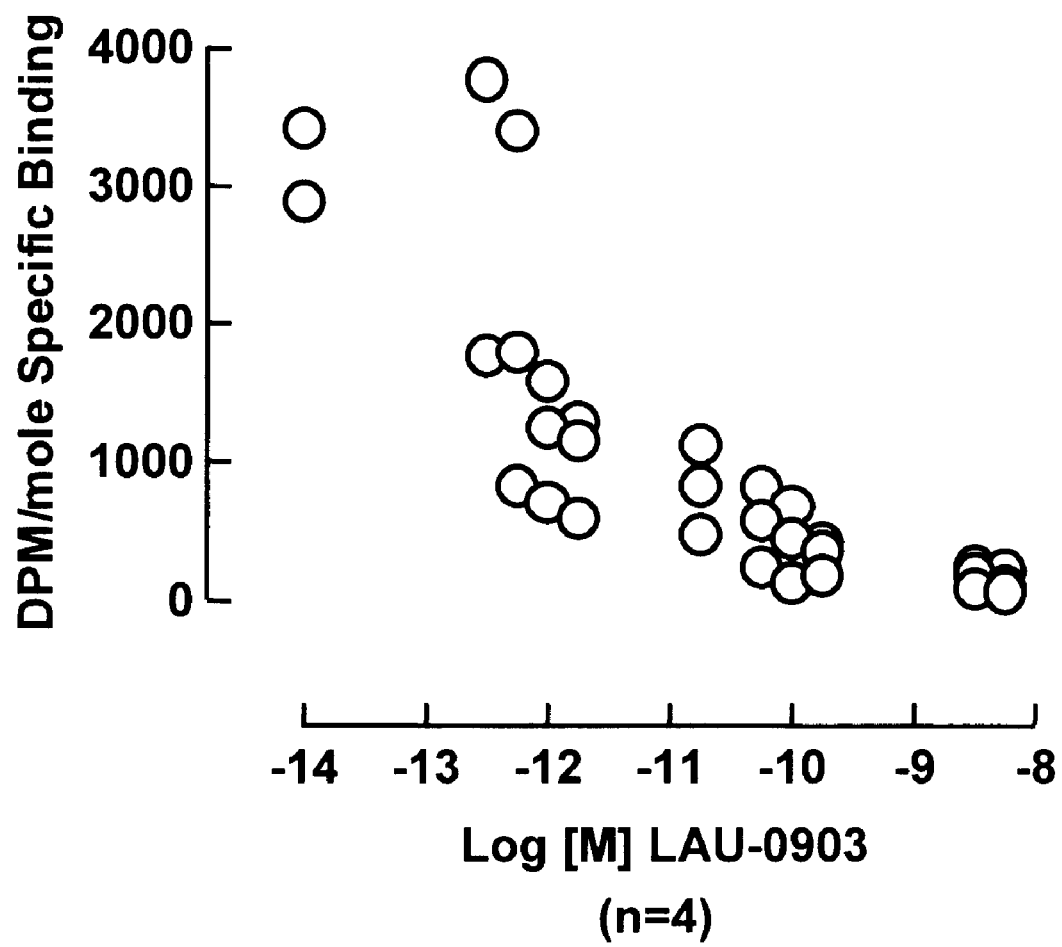
FIG. 3 illustrates the competition by LAU-0903 for $^3$H-PAF (platelet-activating factor) binding to CHO-B cell homogenates.
Figure 4:
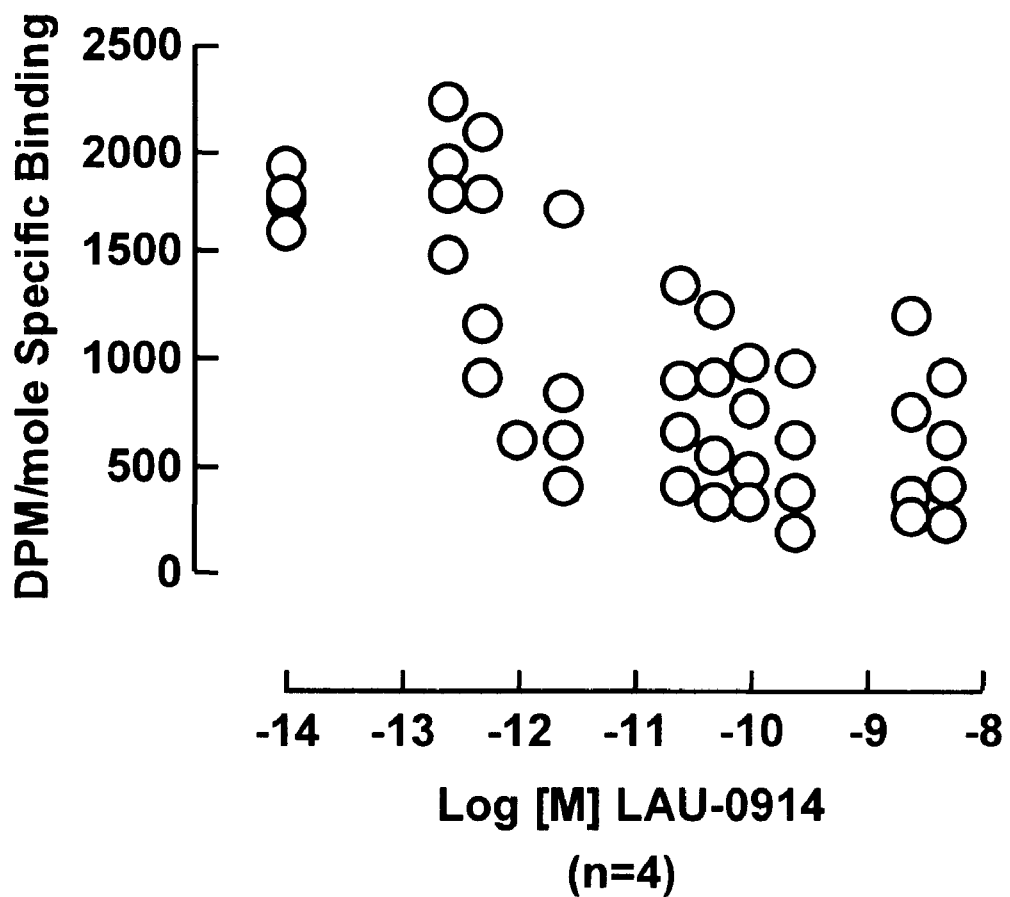
FIG. 4 illustrates the competition by LAU-0914 for $^3$H-PAF (platelet-activating factor) binding to CHO-B cell homogenates.

FIGS. 3 and 4 show the results of competition experiments using LAU-0903 (FIG. 3) and LAU-0914 (FIG. 4) on the binding of $^3$H-PAF to the CHO-B cell homogenate receptors. CHO-B cells are known to overly express a low-affinity PAF receptor (K$_d$: 1.5×10$^{-10}$ M). In FIG. 3, the curve is a single-step sigmoidal curve, indicating a significant displacement by LAU-0903, with an IC$_{50}$ in the range of 5.379×10$^{-11}$ M. In FIG. 4, although a trend toward a single-step sigmoidal curve was seen with LAU-0914, indicating an IC$_{50}$ in the range of 1.625×10$^{-11}$ M, the displacement was not significant because of high dispersion of the points. These data suggest that LAU-0914 is a selective antagonist for the high-affinity binding site found on the microsomal.

Thus, within the LAU-0900 series compounds, the compounds may show different displacement activity, as shown above for LAU-0903 and LAU-0914. LAU-0903 exhibited broad inhibitory activity, and LAU-0914 exhibited selective inhibitory activity for the high-affinity binding site of the PAF receptor in rat brain microsomal preparations.

EXAMPLE 16

LAU-0900 Series Compounds Inhibit ERK and JNK Activation

Stress-sensitive protein kinases are mediators of multiple signaling pathways engaged in cell injury. PAF activates these protein kinases (Mukherjee et al., 1999; DeCoster et al., "Platelet-activating factor is a downstream messenger of kainate-induced activation of mitogen-activated protein kinases in primary hippocampal neurons," J. Neurosci. Res., vol. 53, pp. 297–303 (1998). Two enzymes known to be activated by PAF are c-jun aminoterminal protein kinase ("JNK") and an extracellular regulated kinase ("ERK").

Experimental Protocol: HEK-293 cells (transformed primary human embryo kidney cells, ATCC# CRL-1573) were cultured to confluency in DMEM-10% FBS high-glucose medium (GIBCO-BRL, Rockville, Md). Cells were cultured in 6-well plates and were treated with PAF (100 nM) for 60 min or interleukin-1β ("IL-1β"; 10 ng/ml) for 30 min, and then frozen for later assays for JNK and ERK as described below. To test the effect of compounds of the LAU-0900 series, HEK-293 cells were treated for 30 min with various concentrations (from 10 nM to 1 μM) of the experimental LAU-0900 series compound before the addition of PAF or IL-1β.

In vitro immunocomplex protein kinase assay: Frozen HEK-293 cells treated as described above were homogenized in kinase homogenization buffer (50 mM Tris-HCl, pH 7.0, 250 mM MgCl$_2$, 10 mM NaVaO$_3$, 0.1 M β-glycerophosphate, 0.2 PMSF (Sigma, St. Louis, Mo.), then centrifuged at 2800×g for 15 min at 4° C. The supernatant was removed, and a Triton-X soluble protein lystate prepared for immuno precipitation with antibodies against JNK and ERK kinases (Santa Cruz Biotech., Santa Cruz, Calif.). This lysate was pre-cleaned with protein-A agarose (Boehringer Mannheim), and then incubated with 1:100 dliutions of anti-NIK antibody and anti-I$_k$B-β antibody for 2 hr at 4° C. Triton X-soluble protein lysates were pre-cleaned with protein A-agarose (Boehringer Mannheim), and then incubated with 1:100 dilutions of anti-NIK (NF-kappa-B-induced kinase) antibody and anti-IkB-β antibody for 2 hr at 4° C. Immunoprecipitates were washed once with homogenization buffer and once with kinase buffer (25 mM HEPES, pH 7.4, 20 mM MgCl$_2$, 20 mM glycerophosphate, 10 mM sodium orthovanadate, and 2 mM dithiothreitol).

To measure the JNK activity, aliquots of 5 μg immunoprecipitates were incubated for 30 min at 30° C. using 10 μg GST-cJUN (Santa Cruz Biotechnology, Santa Cruz, Calif.) as substrate. For ERK activity, MBP (myelin basic protein; Sigma ) was used as substrate in combinatio with 20 μM $^{32}$P-ATP (3 μCi, at 10 Ci/mM, Amersham Pharmacia Biotech) in 40 μl kinase buffer as described above. The reactions were terminated by spotting 20 μl of sample onto P81 filter paper squares (Whatman). The filter papers were washed twice with 10 mL per square 1% phosphoric acid, followed by one wash with water. $^{32}$P on the filter paper was counted in a scintillation counter to quantify the phosphorylation of substrate proteins.

Figure 5A:
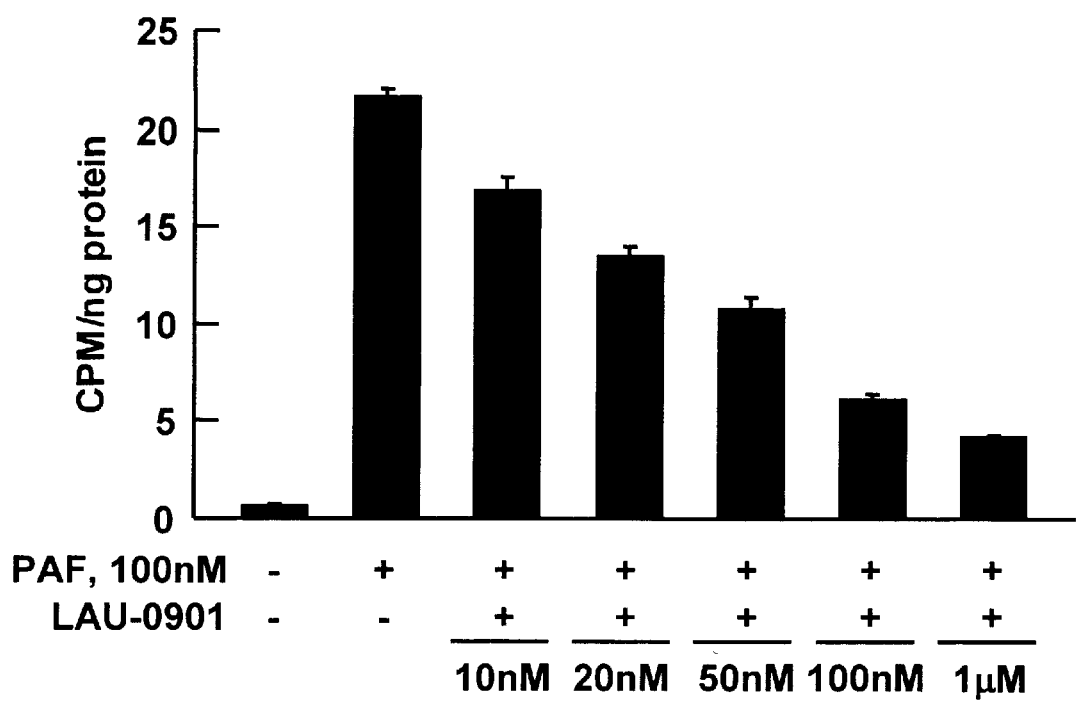
FIG. 5a illustrates the inhibition by various concentrations of LAU-0901 of PAF-mediated c-jun aminoterminal protein kinase ("JNK") activation in human epidermal cells.
Figure 5B:
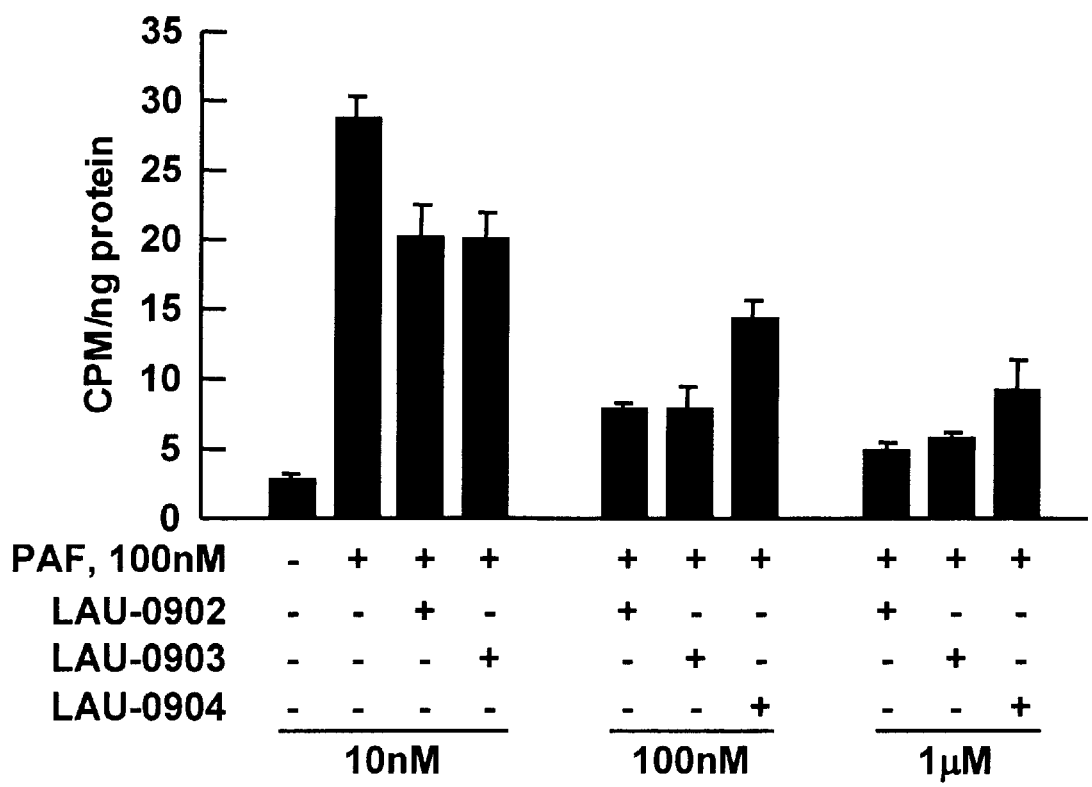
FIG. 5b illustrates the inhibition by various concentrations of LAU-0902, LAU-0903, and LAU-0904 of PAF-mediated c-jun aminoterminal protein kinase ("JNK") activation in human epidermal cells.

FIG. 5a indicates that LAU-0901 inhibited the PAF-induced expression of JNK at concentrations as low as 10 nM. The degree of inhibition was directly related to concentration of LAU-0901. FIG. 5b illustrates that similar inhibition patterns for expression of JNK were seen with LAU-0902, LAU-0903, and LAU-0904.

Figure 6:
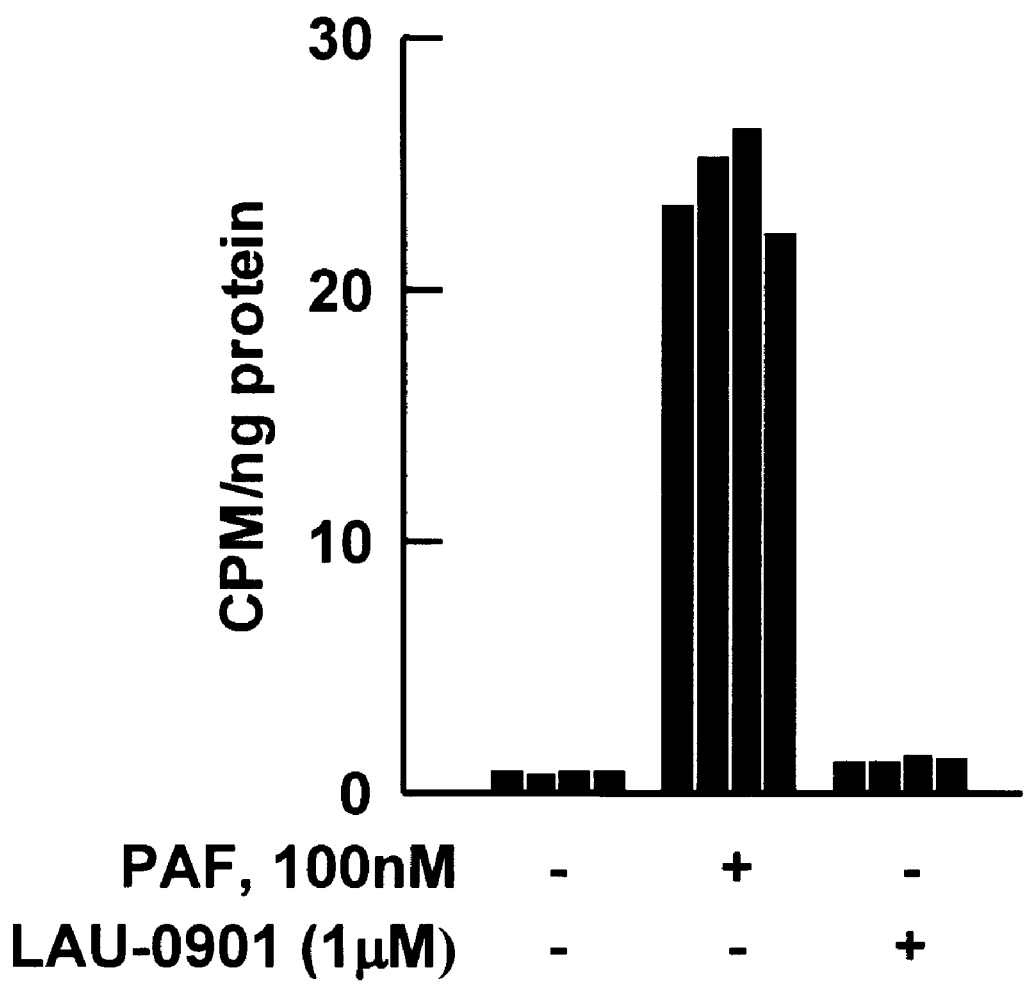
FIG. 6 illustrates the inhibition by LAU-0901 (1 $\mu$M) of PAF-mediated extracellular regulated kinase ("ERK") activation in human epidermal cells.

FIG. 6 illustrates that LAU-0901 inhibited PAF-mediated ERK activation in the HEK-293 cells. Experimental conditions were as described above, except only one concentration, 1 μM, of LAU-0901 was used.

Thus, all tested compounds of the LAU-0900 series (LAU-0901, LAU-0902, LAU-0903, and LAU-0904) inhibited the PAF-activation of JNK expression. Only one LAU-0900 series compound (LAU-0901) was tested for inhibition of ERK expression, and that compound found active. It is believed that other LAU-0900 compounds will inhibit the PAF-activated expression of these two enzymes, JNK and ERK.

EXAMPLE 17

LAU-0900 Series Compounds Inhibit COX-2 Transcription

COX-2 is a mediator of the inflammatory response and of cell injury. See Bazan et al., 1996; N. Bazan, "COX-2 as a multifunctional neuronal modulator," Nat. Med., vol. 7, pp. 414–415 (2001). PAF action mediated through intracellular receptors is involved in the transcriptional activation of the inducible cyclooxygenase-2 (COX-2), which participates in neuroinflammatory responses. (Bazan et al, 1994). IL1-β0 also activates COX-2 expression. See Lukiw et al., "Budesonide epimer R or dexamethasone selectively inhibit PAF- or IL-1β-induced DNA-binding activity of cis-acting transcription factors and cyclooxygenase-2 gene expression in human epidermal keratinocytes," Proc. Natl. Acad. Sci. USA, vol. 95, pp. 3914–3919 (1998).

To test the ability of LAU-0900 series compounds to inhibit COX-2 expression, a kidney cell line was transiently transfected with the 830-base-pair human COX-2 promoter construct (proximal to the transcription start site) fused to the luciferase gene as a reporter as described below.

Transfection of CV-1 cells with human COX-2promoterfused with LUC: C V-1 Cells (African green monkey kidney cell line, ATCC # CCL-17) were grown in DMEM-F12 (GIBCO-BRL, Rockville, Md.) supplemented with 10% FBS (fetal bovine serum) in 6-well plates. At 80% confluence, the cells were transfected with 10 $\mu$g human COX-2 promoter-LUC construct (containing 830 base pairs of the human COX-2 promoter (donated by Dr. Stephen Prescot, Huntsman Cancer Institute, Salt Lake City, Utah) using a liposomal transfection reagent (DOTAP, Roche Diagnostics, Gmbh, Mannheim, Germany). Promoterless β-galactosidase construct (Promega, Madison, Wis.) was co-transfected to assess transfection efficiency. Three hours after transfection at 37° C., the medium was removed, and the cells were washed with phonsphate-buffered saline solution, pH 7.2 (PBS; Gibco-BRL, Rockville Md. The plates were further incubated at 37° C. in complete medium DMEM-F12 with 10% FBS for about 8–10 hr. Before the addition of the inducers of COX-2, PAF (100 nM) or IL-1β (10 ng/ml), the CV-1-transfected cells were serum-starved for 8 hr at 37° C. After the addition of the inducers, the cells were incubated for 8–10 hr at 37° C. Then the medium was removed, the cells were washed with PBS, harvested, and frozen at –80° C. until used for assays.

To test the effectiveness of the LAU-0900 series compounds, the transfected cells were treated for 1 hr with 100 nM of various LAU-0900 series compounds before the addition of the inducers (either PAF or IL-1β, and the LAU-0900 compound remained in the medium throughout the incubation period.

Luciferase assay of transfected CV-1 cells: Frozen cells were homogenized in 300 $\mu$l luciferase assay buffer ("ALL", Analytical Luminescence Laboratory, San Diego, Calif.), and cellular debris was collected as a pellet by centrifugation at 2800×g for 20 min at 4° C. Supernatants (20–30 $\mu$l) were normalized to 1 $\mu$g/ml of total protein content, and were mixed with 70–80 $\mu$l ALL buffer. Reactions were initiated by injection of 100 $\mu$l of 1 mM luciferin (Sigma Chemical Co., St. Louis, Mo.). The relative light units were determined by using an ALL luminometer that recorded over 20-second intervals.

Figure 7:
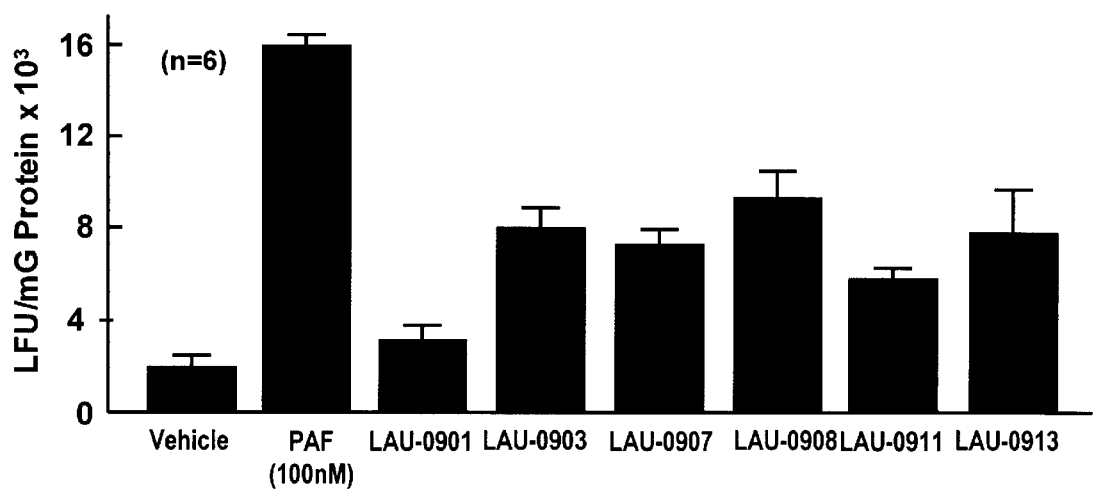
FIG. 7 illustrates the inhibition at 100 nM concentration of the LAU-0900 series compounds (LAU-0901, LAU-0903, LAU-0907, LAU-0908, LAU-0911, and LAU-0913) of PAF-mediated (100 nM PAF) activation of cyclooxygenase-2 ("COX-2").

FIG. 7 indicates that at a concentration of 100 nM, all LAU-0900 series compounds tested (LAU-0901, LAU-0903, LAU-0907, LAU-0908, LAU-0911, and LAU-0913) inhibited COX-2 transcription induced by 100 nM PAF, with LAU-0901 being the most effective inhibitory compound.

Figure 8:
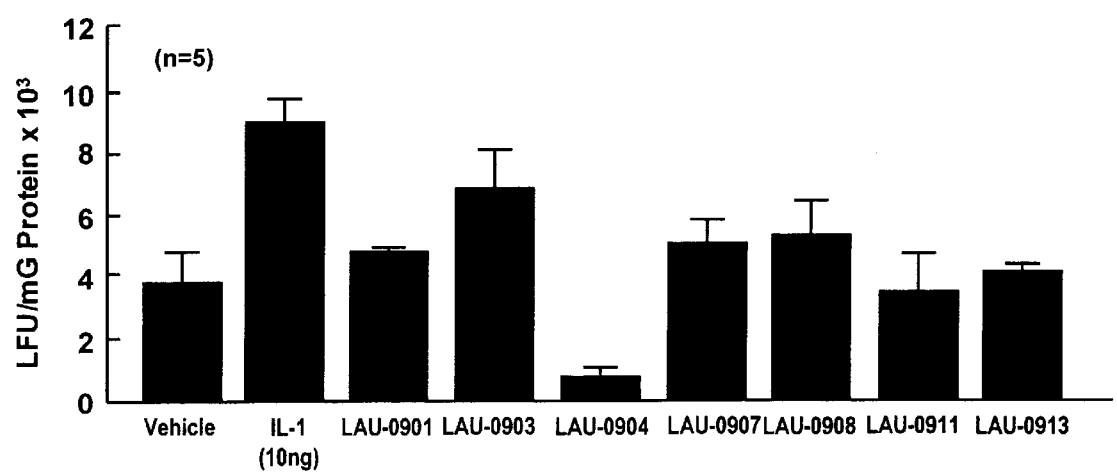
FIG. 8 illustrates the inhibition by 100 nM concentration of the LAU-0900 series compounds (LAU-0901, LAU-0903, LAU-0904, LAU-0907, LAU-0908, LAU-0911, and LAU-0913) of interleukin-1("IL-1")-mediated (10 ng) activation of cyclooxygenase-2 ("COX-2").

FIG. 8 indicates that at a concentration of 100 nM, all LAU-0900 series compounds tested (LAU-0901, LAU-0903, LAU-0904, LAU-0907, LAU-0908, LAU-0911, and LAU-0913) inhibited COX-2 transcription induced by 10 nM IL-1β, with LAU-0904 being the most effective inhibitory compound.

EXAMPLE 18

LAU-900 Series Compounds Are Not Hepatotoxic as Compared with Acetaminophen To assess aspects of in vivo toxicity, serum activities of glutamic oxalacetic transaminase (GOT) and glutamic pyruvic transaminase (GPT) were assayed after 24 hours of "per os" administration of 560 mg/kg LAU-0903 and compared with a comparable amount of a known toxin, acetominophin.

C57-bl/6 mice, 20 to 25 g body weight, purchased from a commercial breeder (Charles River Laboratory, Wilmington, Mass.) were fasted overnight. Either acetaminophen (as Paracetamol, Sigma Chemical Co., St. Louis, Mo.) or LAU-0903 in corn oil were administered "per os" using an esophageal cannula. The dosages were equivalent to the known $LD_{50}$ of acetaminophen: 560 mg/kg concentration. After 24 hours of treatment, the mice were killed, and the blood collected for enzymatic analysis. Assays for GPT or GOT plasma activities were obtained with a kit for transaminase assays (Sigma Chemical Co.).

Figure 9:
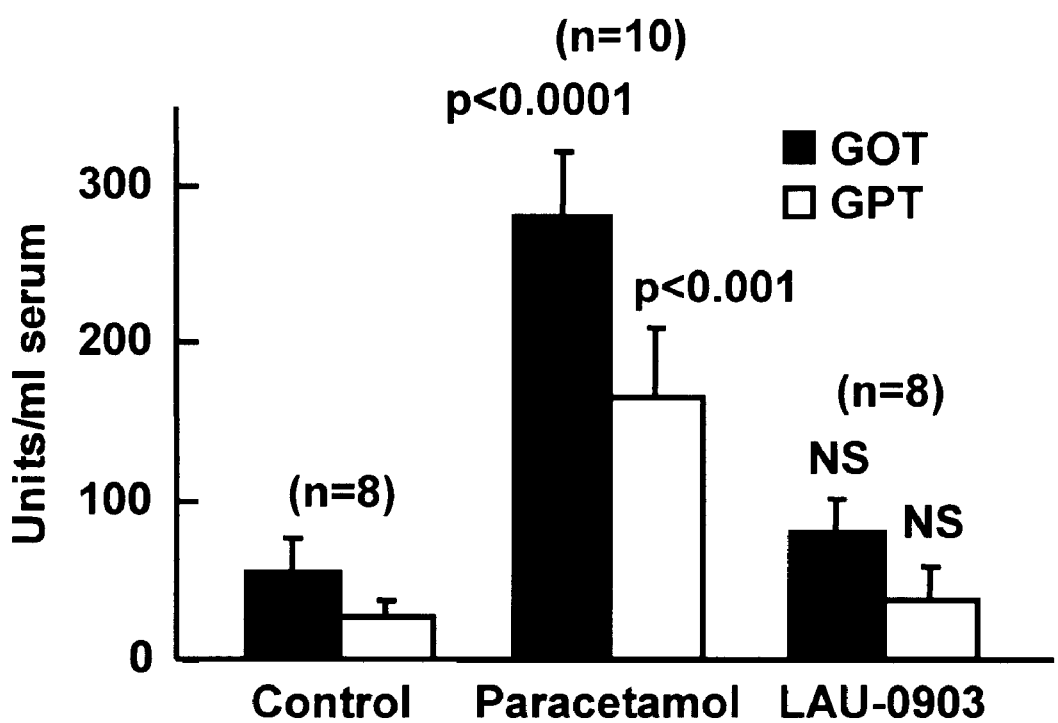
FIG. 9 illustrates a comparison between a similar concentration (560 mg/kg body weight) of p-acetominophen (Paracetamol) and LAU-0903 on the increase in serum activity of glutamic oxalacetic transaminase (GOT) and glutamic pyruvic transaminase (GPT) (high activity indicates liver damage) 24 hr after mice were administered the compounds.

The results are presented in FIG. 9, with the bars representing the mean ±SD for 8 mice for both the control and the LAU-0903 group. The acetaminophen-treated group contained 10 mice. As shown in FIG. 9, acetaminophen significantly increased the GOT and GPT serum levels. However, LAU-903 did not significantly change the serum level of either enzyme indicating less toxicity, at least by this measure.

EXAMPLE 19

Some LAU-0900 Series Compounds Decrease Oxidative Stress-Induced Cell Death To test the effectiveness of the LAU-0900 series compounds as inhibitors of oxidative stress-induced cell death, human retinal pigment epithelial cells in culture (ARPE-19 cells, ATCC #CRL-2302) were used. ARPE-19 cells were cultured to confluence in DMEM-10% FBS medium (Gibco-BRL). The cells were then divided into 11 groups. Nine groups were exposed overnight to 100 mM of a test compound selected from LAU-0901, LAU-0903, LAU-0904, LAU-0905, LAU-0906, LAU-0907, LAU-0908, LAU-0909, and LAU-0910. The other two groups were control groups, and were not exposed to any test chemical. In the nine groups and in one control group, oxidative stress was triggered by the addition of a combination of tumor necrosis factor ("TNF"; 10 ng/ml) and hydrogen peroxide ("$H_2O_2$"; 1.6 $\mu$M). The second control group was not treated with TNF and $H_2O_2$.

In the presence of TNF and $H_2O_2$, extensive Hoechst positivity was seen in the control group, while no staining was found in the control group not exposed to TNF and $H_2O_2$. (Data not shown.) These results confirmed that TNF and $H_2O_2$ induced oxidative stress cell death as indicated by Hoechst positivity staining. In the cells that had been previously exposed to the LAU-0900 series compounds, a lesser degree of Hoechst staining was seen indicating that the LAU-0900 series compounds had elicited cytoprotection. The amount of Hoeschst staining was least in the group treated with LAU-0901, and most in the group treated with LAU-0910.

EXAMPLE 20

LAU-0903 Decreases Vasogenic Cerebral Edema-Induced COX-2 Expression

Brain COX-2 gene expression is known to be enhanced as a result of injury as well as by seizures (Marcheselli and Bazan, 1996), and PAF receptors are involved in COX-2 expression (Bazan et al, 1994). To further test the LAU-0900 series compounds as PAF antagonists, the compounds were tested in an in vivo model for the potential blocking of injury-induced COX-2 induction. Adult Sprague-Dawley rats, 175 to 250 g body weight, were purchased from a commercial breeder (Charles River Laboratories, Wilmington, Mass.). One group of four rats received an intra-cerebroventricular injection of LAU-0903 (10 mg/kg in DMSO as a vehicle), 15 min before the generation of cerebral edema. Another group of four rats received an intraperitoneal injection of desxmethasone every 8 hr for a period of 24 hr prior to injury. Animals were immobilized by ether anesthesia, and vasogenic cerebral edema was generated by the application of a liquid nitrogen-cooled probe for 1 min on the parietal region of the skull. The rats were allowed to recover for either 2 or 6 hr before being decapitated to sample the brain. Total brain tissues were obtained, and total-RNA was extracted. The RNA was then assayed by Northern blot analysis for COX-2 mRNA. Total RNA was extracted and purified using the guanidinium-thiocyanate-phenol-chloroform method of P. Chomezynski and N. Sacchi, "Single-step method of RNA isolation by acid guanidinium thiocyanate-phenol-chloroform extraction," Anal. Biochem., vol. 162, pp. 156–159 (1987). Gel electrophoresis of total-RNA (5 $\mu$g/lane) was performed under denaturing conditions on a 1.2% agarose gel. RNA was transferred to Hybond-N nylon membranes (Amersham, Arlington, Hieghts, Ill.), followed by hybridization at 42 C. with $^{32}$P-labelled DNA probes for COX-2, Zif-268, and GAPDH (Molecular Dynamics, Sunnyvale, Calif.). $^{32}$P-labelled DNA probes for COX-2, Zif-268, and GAPDH were obtained by random primer extension from cDNA inserts. See D. A. Kujubu et al., "Dexamethasone inhibits mitogen induction of the TIS10 prostaglandin synthase/cyclooxygenase gene," J. Biol. Chem., vol. 267, pp. 7991–7994 (1992); J. Milbrandt, "A nerve growth-factor induced gene encodes a possible transcriptional regulatory factor," Science, vol. 238, pp. 797–799 (1987); and J. Y. Tso et al., "Isolation and characterization of rat and human glyceraldehyde-3-phosphate dehydrogenase cDNAs: genomic complexity and molecular evolution of the gene," Nucleic Acids Res., vol. 13, pp. 2485–2502 (1985). Autoradiography or phosphorimage quantification was performed.

Figure 10:
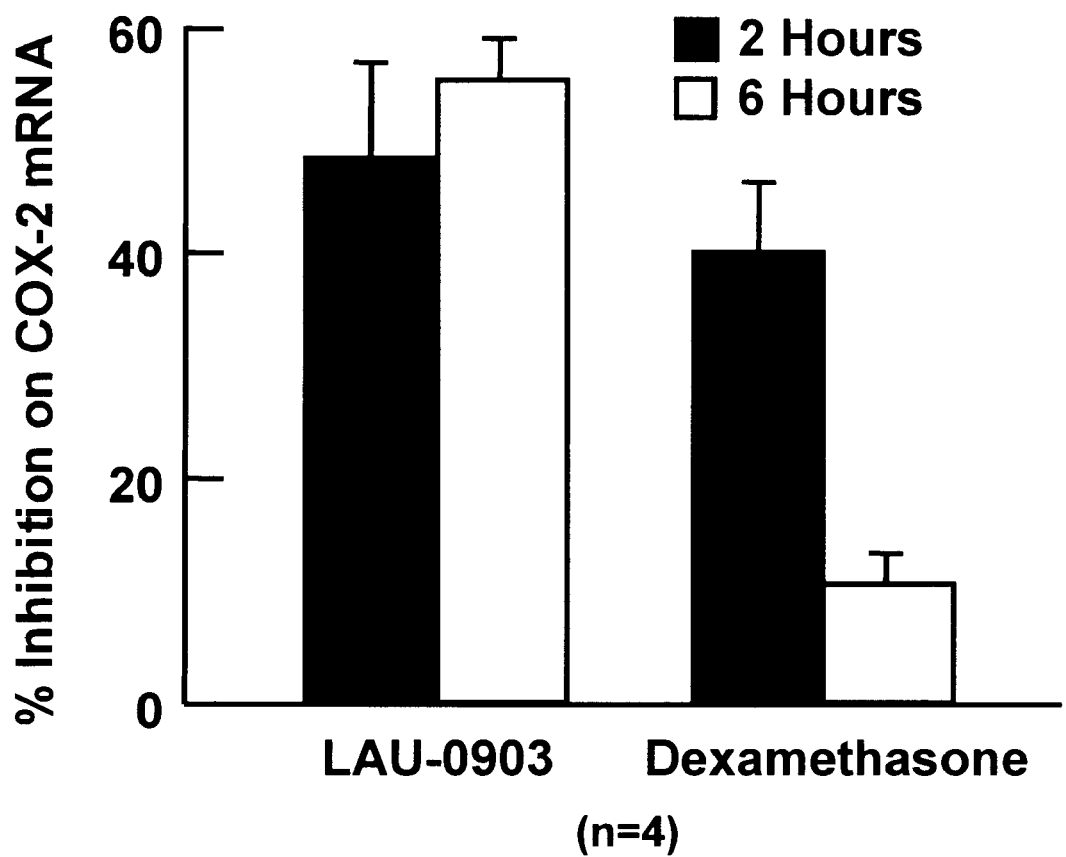
FIG. 10 illustrates the comparative inhibition of LAU-0903 (10 mg/kg, administered 15 minutes prior to the injury) and the steroid dexamethasone (10 mg/kg delivered by three intravenous injections every 8 hr for 24 hr prior to injury) on the expression levels of COX-2 mRNA after cryogenic injury of a rat brain.

FIG. 10 shows a comparison of the effects of the prior injection of LAU-0903 or of dexamethasone on the expression levels of COX-2 mRNA after cryogenic injury of the ratbrain. The data shown are means +/− SD of four individuals, expressed as a percent inhibition of cryogenically induced expression levels of COX-2 mRNA.

As shown in FIG. 10, the injection of LAU-0903 caused more than 50% inhibition of COX-2 mRNA, performing better than dexamethasone, a well known steroid that inhibits gene expression. Moreover, the inhibition by LAU-0903 was sustained for up to 6 hours after a single injection, unlike the effect of dexamethasone.

EXAMPLE 21

Protective Effect of LAU-0903 on Vasogenic Cerebral Edema

To further test the protective effect of LAU-0903 during cerebral edema, 30 $\mu$g/kg body weight of LAU-0903 (solubilized in DMSO) was injected intra-ventricularly 15 min before induction of injury. In another group of mice, 6.2 $\mu$g/kg bodyweight of dexamethasone was injected intraperitonealy every 8 hr for 24 hr before injury, as described above in Example 20. The extent of brain damage was assessed by the amount of brain tissue that was stained with Evans Blue (saline solution, 2%, 0.5 ml/rat), which was injected intravenously into the animals 2 hr before the injury. Under conditions of vasogenic injury or edema, Evans Blue leaks from the blood vessels into brain tissue, and accumulates in the brain proportionally to the degree of injury. Tiuue samples and blood samples were individually homogenized in 1 mL of 50% trichloroacetic acid. Homogenates were recovered and subjected to 10,000 rpm centrifugation to remove insoluble particulates. Samples were then mixed in 3 volumes of pure ethanol, and stored for fluorescence detection. Evans Blue quantitative analysis was performed on an high-performance liquid chromotography (HPLC) system connected to a fluorescence detector (Beckman, Palo Alto, Calif.). Detection was performed using a 620 nm excitation wavelength (10 nm band witdth), and a 680 nm emission wavelength (10 nm band with). The HPLC pump was set at 2 ml/min, and the solvent was %0% trichloroacetic acid: methanol (25:75). Data were recorded and a ratio calculated of ($\mu$g EB brain/mg brain protein)/($\mu$g EB blood/$\mu$g blood protein) to correct for any differences in Evans blue clearance.

Figure 11:
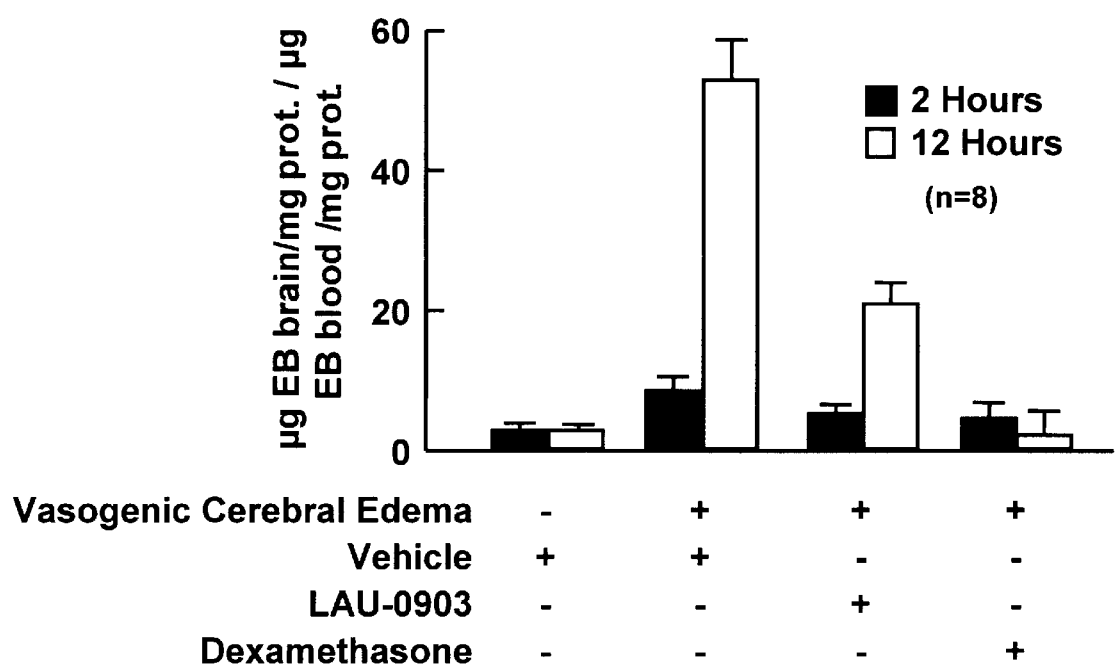
FIG. 11 illustrates the comparative inhibition of LAU-0903 (10 mg/kg) and dexamethasone (10 mg/kg) on the extravascular accumulation of Evans blue dye in the rat brain cortex at 2 hr and 12 hr after cryogenic injury, when the compounds were administered 15 min prior to the injury.

FIG. 11 shows the mean +/− S.D. for eight animals for the various treatments. LAU-0903 was shown to have a protective effect on the accumulation of Evans Blue in the brain cortex of the rat as result of the vasogenic cerebral edema. However, in this experiment, dexamethasone produced more of a protective effect than did LAU-0903, especially after 12 hr.

EXAMPLE 22

Neuroprotection by LAU-0900 Series in a Mouse Model of Stroke: Middle Cerebral Artery Occlusion (MCA-O)

To test the neuroprotective activity of the LAU-0900 series compounds, middle cerebral artery occlusion ("MCA-O") was performed on C57BL/6 mice (20 to 25 g body weight; Charles River Laboratories, Wilmington, Mass.) as a model of brain damage due to stroke. The mice were housed for at least 24 hr after arrival and given water and food ad libitum. All protocols and surgical procedures were in accordance with both local and NIH guidelines. The mice were anesthetized with 3.5% halothane in a mixture of 70% nitrous oxide and 30% oxygen, and were maintained anesthetized with % halothane in the same nitrous oxide/oxygen mixture. The mouse body temperature was kept at 36.5–37.5° C. with a Harvard homeothermic blanket. The common carotid and external carotid arteries were separated from surrounding tissues in the ventral region of the neck, and the external carotid artery was occluded just proximal to its bifurcation. The common carotid was temporarily occluded with a retracting suture, and then the external carotid artery was sectioned. An occluding filament (heat blunted 6-0 monofilament nylon suture) was introduced into the sectioned external carotid artery and advanced to the common carotid artery. The occluding filament was redirected into the internal carotid artery, and advanced until the blunted tip entered the anterior cerebral artery and until the side of the filament occluded the origin of the middle cerebral artery. The stump of the external carotid artery was ligated, holding the occluding filament in place. The clamp to common carotid artery was gently removed, restoring blood flow to the carotid system. All retracting sutures were removed, and the wound was closed with three interrupted silk sutures. The animals were allowed to recover from anesthesia.

When fully awake, the mice were tested for neurological scores before returning to their holding cages. See J. B. Bederson et al, "Rat middle cerebral artery occlusion: evaluation of the model and development of a neurologic examination," Stroke, vol. 17, pp.472–476 (1986). Mice not performing at least a class 2 score (circling to the left, indicating sizable infarct) were discarded Occlusion was maintained for 120 min, and then blood perfusion was reinstated by careful removal of the occluding filament under anesthesia. To maintain body temperature through recovery, mice were kept in cages over thermal pads in a temperature-controlled recovery room at 25–27° C.

Mice were killed in a $CO_2$ chamber, and the brain rapidly dissected out. The brain was chilled on ice and embedded in 3% agar block. Serial coronal sections 1 mm thick were obtained with a Rotor slicer (Ted Pella, Inc.; Redding, Calif.). The 1 mm sections were placed in a 2% 2,3,5-tryphenyltetrazolium chloride ("TTC") staining solution (Sigma Chemical, St. Louis, Mo.), and incubated at 37° C. for 30 min. Images from the serial sections were captured with a Sony DXC-960MD 3 CCD color video camera installed on a Nikon SMZ-U dissection microscope at 2×final magnification. Digitalized images were stored on a computer for processing by Adobe Photoshop. A quantitative volume of the infarcted regions for each mouse was obtained by serial densitometry of the sections.

FIGS. 12a, 12b, and 12c show the results with the data expressed as a % infarction after MCA-O. The volumetric analysis of infarcted regions was obtained after 24-h reperfusion.

In FIG. 12a, either LAU-0901 (30 mg/kg) or vehicle was injected intraperitoneally 1 h before the MCA-O operation. MCA-O was maintained for 1 hr. Mice were killed 24 hr after treatment, and the % infarction compared. Significant reduction of the infarcted volume (55%) was obtained when animals were treated 1 hr before MCA-O with LAU-0901.

In FIG. 12b, either LAU-0901 (30 mg/kg) or vehicle was injected at the onset of MCA-O. MCA-O was maintained for 1 hr. Again, the mice were killed 24 hr later. When LAU-0901 was delivered at the onset of MCA-O, a 40% reduction of infarcted volume was obtained.

In FIG. 12c, either LAU-0901, LAU-0904, or LAU-0911 (30 mg/kg) was injected 1 hr after reperfusion following 1 hr of MCA-O to determine whether the compound would still exert a protective effect. For all three LAU-0900 series compounds, the infarcted volume was reduced by 40% even though the injection was 1 hr after reperfusion was initiated.

In a second group of experiments, C57-bl/6 mice were treated with either a sham procedure, or with 1 hr with MCA-O followed by a reperfusion period of 21 days. Cresil-violet staining was used to assess brain damage in brain slices obtained as above. The mice treated with the sham procedure did not display any brain damage in the sections. (Data not shown.). The MCA-O mice treated with only vehicle showed extensive brain damage after 21 days. (Data not shown).

In a third set of experiments, the MCA-O treated mice were injected once with the LAU-0900 series compounds (LAU-0901, LAU-0904, and LAU-0911; at 30 mg/kg) or vehicle 1 hr after the onset of reperfusion. The LAU-0900 compounds were solubilized in 45% 2-hydroxypropyl-β-cyclodextrine (Sigma Chemical Co.), and delivered intraperitoneally. The mice were reperfused for 21 days, and killed. Coronal sections of mouse brains were processed for histology, and stained with Cresil-Violet. Sections from individual animals were analyzed, with pictures of the right side (infarcted) of the brain compared to the left side, which show almost no damage.

LAU-0901, LAU-0904, and LAU-0911 displayed significant protection as compared with vehicle-treated animals. (Data not shown). Substantial differences were obvious in the middle cerebral artery territory of the right brain (the occluded side), where dramatic reduction in nuclei counts and enhanced injury were observed in the vehicle-treated animals as a consequence of 1-hour MCA-O. The hippocampus showed the most pronounced differences, with an almost complete loss of the CA3 and CA2 regions. CA1 also showed damage although to a lesser extent. The dentate gyrus showed reduced cell numbers, and most of the remaining cells had condensed nuclei, an indication that they may have been undergoing apoptosis. Almost normal morphology was found in the brains of the LAU-0900-treated animals, indicating a high degree of protection. (Data not shown), even though administered 1 hr after the initiation of reperfusion.

As shown in the above experiments, all LAU-0900 series compounds tested had some activity as a PAF-antagonist. LAU-0912 was the only compound not tested to date. However, it is believed that it will also be effective as a PAF-antagonist because of its structural similarity with other LAU-0900 series compounds, especially LAU-0911, that showed activity.

The complete disclosures of all references cited in this specification are hereby incorporated by reference. Also, incorporated by reference is N. G. Bazan, Carlos Sunkel, Victor Marcheselli, and Julio Alvarez-Builla, "LAU-0900 Series: Novel Neurprotective Compounds," a manuscript to be submitted to the J. Med. Chem. In the event of an otherwise irreconcilable conflict, however, the present specification shall control.

We claim:

1. A compound having the structure

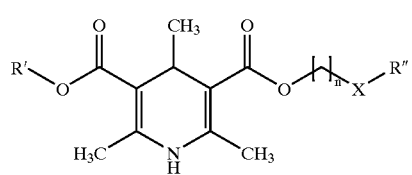

or a pharmaceutically acceptable salt thereof, wherein:

R' is a methyl group or 1,3-di-(4-morpholinyl)-2-propyl;

R" is 3,4-dichlorophenyl; 4-fluorophenyl; 4-imidazol-1-phenyl; 4-propoxyphenyl; 4-butoxyphenyl; 4-(3-oxo-buten-1-yl)phenyl; 3,4,5-trimethoxyphenyl; 4-butyryl phenyl; or 4-methoxyiminomethylphenyl;

n is 2 or 3; and

X is an atom of oxygen or sulfur.

2. The compound of claim 1 wherein R' is 1,3-di-(4-morpholinyl)-2-propyl.

3. A compound of claim 2 which is 2,4,6-trimethyl-1,4-dihydro-pyridine-3,5-dicarboxylic acid 5-[2-(3,4-dichloro phenoxy)]ethyl ester 3-[1,3-di-(4-morpholinyl)]-2-propyl-1-ester dihydrochloride (LAU-0901), or a pharmaceutically acceptable salt thereof.

4. The compound of claim 1 wherein R' is methyl.

5. A compound of claim 4 which is 2,4,6-trimethyl-1,4-dihydro-pyridine-3,5-dicarboxylic acid 5-[3-(4-fluorophenysulfanyl)]-propyl-1-ester 3-methyl ester (LAU-0904), or a pharmaceutically acceptable salt thereof.

6. A compound of claim 4 which is 2,4,6-trimethyl-1,4-dihydro-pyridine-3,5-dicarboxylic acid 5-[3-(4-imidazol-1-yl-phenoxy)]-propyl-1-ester 3-methyl ester (LAU-0902), or a pharmaceutically acceptable salt thereof.

7. A compound of claim 4 which is 2,4,6-trimethyl-1,4-dihydro-pyridine-3,5-dicarboxylic acid 5-[3-(imidazol-1-yl-phenylsulfanyl)]-propyl-1-ester 3-methyl ester (LAU-0903), or a pharmaceutically acceptable salt thereof.

8. A compound of claim 4 which is 2,4,6-trimethyl-1,4-dihydro-pyridine-3,5-dicarboxylic acid 5-[3-(4-butoxyphenylsulfanyl)]-propyl-1-ester 3-methyl ester (LAU-0905), or a pharmaceutically acceptable salt thereof.

9. A compound of claim 4 which is 2,4,6-trimethyl-1,4-dihydro-pyridine-3,5-dicarboxylic acid 5-[3-(4-propoxyphenylsulfanyl)]-propyl-1-ester 3-methyl ester (LAU-0907) or a pharmaceutically acceptable salt thereof.

10. A compound of claim 4 which is 2,4,6-trimethyl-1,4-dihydropyridine-3,5-dicarboxylic acid 3-[3-(4-butoxyphenoxy)propyl]ester 5-methyl ester (LAU-0910), or a pharmaceutically acceptable salt thereof.

11. A compound of claim 4 which is 2,4,6-trimethyl-1,4-dihydro-pyridine-3,5-dicarboxylic acid 5-[4-(3-oxo-but-1-enyl)-phenoxy]-propyl-1-ester 3-methyl ester (LAU-0908), or a pharmaceutically acceptable salt thereof.

12. A compound of claim 4 which is 2,4,6-Trimethyl-1,4-dihydro-pyridine-3,5-dicarboxylic acid 5-(3,4,5-trimethoxyphenoxy)-propyl-1-ester 3-methyl ester (LAU-0911), or a pharmaceutically acceptable salt thereof.

13. A compound of claim 4 which is 2,4,6-trimethyl-1,4-dihydropyridine-3,5-dicarboxylic acid 3-methyl ester 5-[3-(3,4,5-trimethoxyphenylsulfanyl)propyl]ester (LAU-0912), or a pharmaceutically acceptable salt thereof.

14. A compound of claim 4 which is 2,4,6-trimethyl-1,4-dihydro-pyridine-3,5-dicarboxylic acid 5-[3-(4-butyryl-phenoxy)-propyl]1-ester 3-methyl ester (LAU-0913), or a pharmaceutically acceptable salt thereof.

15. A compound of claim 4 which is 2,4,6-trimethyl-1,4-dihydro-pyridine-3,5-dicarboxylic acid 3-{3-[4-(methoxyimino-methyl)-phenoxy]-propyl}ester 5-methyl ester (LAU-0914), or a pharmaceutically acceptable salt thereof.

16. A compound of claim 4 which is 2,4,6-Trimethyl-1,4-dihydro-pyridine-3,5-dicarboxylic acid 5-13-(4-butyryl-phenoxy)-propyl]1-ester 3-methyl ester (LAU-0906), or a pharmaceutically acceptable salt thereof.

17. A compound of claim 4 which is 2,4,6-Trimethyl-1,4-dihydropyridine-3,5-dicarboxylic acid 3-[3-(4-propoxy-phenoxy)propyl]ester 5-methyl ester (LAU-0909), or a pharmaceutically acceptable salt thereof.

18. A pharmaceutical composition comprising an amount of a compound of claim 1, or a pharmaceutically acceptable salt thereof, effective to protect neurons from injury due to activation of platelet-activating factor, and a pharmaceutically acceptable carrier.

19. A method of inhibiting platelet-activating factor which comprises administering to a mammal an effective amount of a compound as recited in claim 1.

20. A method of inhibiting damage to brain neurons that would otherwise result from platelet-activating factor activation, which comprises administering to a mammal an effective amount of a compound as recited in claim 1.

21. A method of inhibiting the expression of COX-2 which comprises administering to a mammal an effective amount of a compound as recited in claim 1.

22. A method to inhibit the expression of c-aminoterminal jun kinase that is mediated by either platelet activating factor or a cytokine which comprises administering to a mammal an effective amount of a compound as recited in claim 1.

23. A method to inhibit the expression of extracellular regulated kinase that is mediated by either platelet activating factor or a cytokine which comprises administering to a mammal an effective amount of a compound as recited in claim 1.

24. A method to decrease cerebral edema resulting from a brain trauma which comprises administering to a mammal an effective amount of a compound as recited in claim 1.

25. A method to inhibit neuronal brain damage resulting from a stroke which comprises administering to a mammal an effective amount of a compound as recited in claim 1.

26. A method of making a compound having the following structure, or a pharmaceutically acceptable salt thereof:

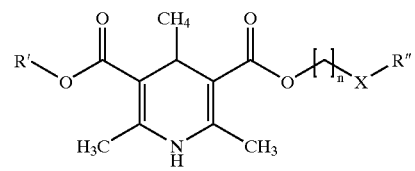

wherein R' is a methyl group or 1,3-di-(4-morpholinyl)-2-propyl;

R" is 3,4-dichlorophenyl; 4-fluorophenyl; 4-imidazol-1-phenyl; 4-propoxyphenyl; 4-butoxyphenyl; 4-(3-oxo-buten-1-yl)phenyl; 3,4,5-trimethoxyphenyl; 4-butyryl phenyl; or 4-methoxyiminomethylphenyl;

n is 2 or 3; and

X is an atom of oxygen or sulfur, wherein said process comprises reacting (1) a compound having the structure as follows:

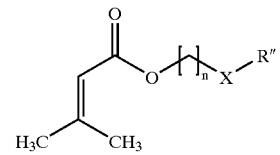

(2) a compound having the structure as follows:

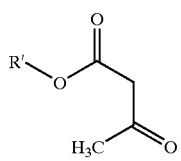

and (3) acetaldehyde.

* * * * *

UNITED STATES PATENT AND TRADEMARK OFFICE
CERTIFICATE OF CORRECTION

| | | |
|---|---|---|
| PATENT NO. | : 6,566,359 B1 | Page 1 of 1 |
| APPLICATION NO. | : 10/151984 | |
| DATED | : May 20, 2003 | |
| INVENTOR(S) | : Nicolas G. Bazan et al. | |

It is certified that error appears in the above-identified patent and that said Letters Patent is hereby corrected as shown below:

In the Specification

At Column 1, Line number 4, add:
--This invention was made with government support under NS023002, and EY005121 awarded by the National Institutes of Health. The government has certain rights in the invention.--

Signed and Sealed this
Twenty-fifth Day of November, 2025

John A. Squires
*Director of the United States Patent and Trademark Office*